US009863885B2

(12) United States Patent
Zaretski et al.

(10) Patent No.: US 9,863,885 B2
(45) Date of Patent: Jan. 9, 2018

(54) GRAPHENE-BASED MULTI-MODAL SENSORS

(71) Applicant: The Regents of the University of California, Oakland, CA (US)

(72) Inventors: Aliaksandr Zaretski, San Diego, CA (US); Darren J. Lipomi, San Diego, CA (US); Alex Savtchenko, Encinitas, CA (US); Elena Molokanova, Encinitas, CA (US); Mark Mercola, La Jolla, CA (US)

(73) Assignee: The Regents of the University of Californa, Oakland, CA (US)

( * ) Notice: Subject to any disclaimer, the term of this patent is extended or adjusted under 35 U.S.C. 154(b) by 0 days.

(21) Appl. No.: 15/288,687

(22) Filed: Oct. 7, 2016

(65) Prior Publication Data

US 2017/0102334 A1    Apr. 13, 2017

Related U.S. Application Data

(60) Provisional application No. 62/238,495, filed on Oct. 7, 2015, provisional application No. 62/238,489, filed on Oct. 7, 2015.

(51) Int. Cl.
*G01N 21/65* (2006.01)
*C23C 14/18* (2006.01)
(Continued)

(52) U.S. Cl.
CPC ........... *G01N 21/658* (2013.01); *C23C 14/18* (2013.01); *C23C 14/30* (2013.01); *C23C 16/01* (2013.01);
(Continued)

(58) Field of Classification Search
CPC .............. G01N 21/658; G01N 27/028; G01N 2021/651; G01L 1/18; C23C 16/0227;
(Continued)

(56) References Cited

U.S. PATENT DOCUMENTS 5,569,506 A * 10/1996 Jahnes ................. C23C 14/165
360/133
9,244,015 B2 * 1/2016 Li ......................... G01N 21/658
(Continued)

OTHER PUBLICATIONS https://en.wikipedia.org/wiki/Plasmonic_nanoparticles.*
(Continued)

*Primary Examiner* — Tarifur Chowdhury
*Assistant Examiner* — Mohamed K Amara
(74) *Attorney, Agent, or Firm* — Fish & Richardson P.C.

(57) ABSTRACT

A method for fabricating a composite film structure, the method includes determining a desired morphology for a metallic layer of the composite film structure, selecting a first metal substrate based on the determining, transferring a graphene layer onto the first metal substrate, depositing the metallic layer on the graphene layer to achieve the desired morphology, and removing the first metal substrate from the graphene and the deposited metallic layer to form the composite film structure. A surface energy difference between the first metal substrate and the deposited metallic layer results in the desired morphology of the metallic layer.

13 Claims, 25 Drawing Sheets

(51) Int. Cl.
*C23C 14/30* (2006.01)
*C23C 16/01* (2006.01)
*C23C 16/02* (2006.01)
*C23C 16/26* (2006.01)
*G01L 1/18* (2006.01)
*G01N 27/02* (2006.01)

(52) U.S. Cl.
CPC .......... *C23C 16/0227* (2013.01); *C23C 16/26* (2013.01); *G01L 1/18* (2013.01); *G01N 27/028* (2013.01); *G01N 2021/651* (2013.01)

(58) Field of Classification Search
CPC ......... C23C 14/18; C23C 16/26; C23C 16/01; C23C 14/30
See application file for complete search history.

(56) References Cited

U.S. PATENT DOCUMENTS

| | | | |
|---|---|---|---|
| 9,279,767 B2* | 3/2016 | Li | G01N 21/648 |
| 2011/0200787 A1 | 8/2011 | Regan et al. | |
| 2013/0056876 A1 | 3/2013 | Harvey et al. | |
| 2013/0120748 A1 | 5/2013 | Li et al. | |
| 2013/0153860 A1 | 6/2013 | Kim et al. | |
| 2013/0210218 A1 | 8/2013 | Accardi et al. | |
| 2014/0147473 A1* | 5/2014 | Yao | H01M 6/40 424/400 |
| 2014/0290565 A1* | 10/2014 | Kim | B01J 23/72 117/94 |
| 2014/0308523 A1* | 10/2014 | Veerasamy | B82Y 30/00 428/408 |
| 2015/0049332 A1* | 2/2015 | Sun | G01N 21/658 356/301 |
| 2015/0136737 A1* | 5/2015 | Loh | B82Y 30/00 216/100 |
| 2015/0155681 A1* | 6/2015 | Ozyilmaz | H01S 3/06791 372/6 |
| 2015/0217219 A1 | 8/2015 | Sinsabaugh et al. | |
| 2015/0293025 A1* | 10/2015 | Ninomiya | C23C 14/562 356/244 |
| 2015/0371848 A1* | 12/2015 | Zaretski | H01L 21/02527 438/496 |
| 2016/0376156 A1* | 12/2016 | Choubak | C01B 31/0453 427/249.1 |
| 2017/0051399 A1* | 2/2017 | Veerasamy | C23C 14/221 |
| 2017/0081782 A1* | 3/2017 | Yoon | C30B 25/186 |
| 2017/0170381 A1* | 6/2017 | Norris | H01L 35/32 |

OTHER PUBLICATIONS

"Gold nanostructures: engineering their plasmonic properties for biomedical applications" to Hu et al, Chem, Soc. Rev. (2006).*
"The surface science of graphene: Metal interfaces, CVD synthesis, nanoribbons, chemical modifications, and defects" to Batzill, Surface Science Reports 67, (2012) 83-115.*
"Wetting transparency of graphene" to Rafiee et al., Nature Materials, (2012), 11, 217-222.*
"Metals on graphene: interactions, growth morphology and Thermal stability", to Liu et al., Cystals (2013), 3, 79-111.*
International Search Report, Application No. PCT/US2016/056016, dated Feb. 7, 2017.

* cited by examiner

GRAPHENE-BASED MULTI-MODAL SENSORS

CROSS-REFERENCE TO RELATED APPLICATIONS

This application claims the benefit of the priority date of U.S. Provisional Patent Application No. 62/238,489, entitled "Graphene-based Multi-Modal Sensors," filed on Oct. 7, 2015, and U.S. Provisional Patent Application No. 62/238, 495, entitled "Graphene-based Multi-Modal Sensors," filed on Oct. 7, 2015. The entire contents of these provisional applications are herein incorporated by reference.

TECHNICAL FIELD

This invention relates to sensors.

BACKGROUND

Graphene has several attractive characteristics. It is flexible and stretchable compared to metallic films, conductive, transparent, amenable to large-area growth and transfer to many substrates, and its crystalline grains can extend over dimensions reaching 1 cm.

SUMMARY

The disclosed multimodal sensors can generate electrical responses to mechanical stimuli (tensile, compressive strains) as well as serve as surface-enhanced Raman scattering (SERS) substrates to evaluate local chemical environments by Raman spectroscopy.

The disclosed sensors and methods herein relate to a strain sensor having unprecedented high sensitivity (gauge factor ~700 at 1% strain), a useful range from 0.001% strain to above 10% strain, and good cyclability.

The disclosed sensors and methods also include graphene-supported SERS substrates deposited onto tips of optical fibers that enable remote Raman sensing applications.

The systems and methods disclosed herein provide the first demonstration of measuring cardiomyocytes contractions using a mechanical strain sensor. By culturing cardiomyocytes on the sensor substrates, it is possible to record and analyze spontaneous and stimulated cardiomyocyte contractions using the sensors and methods disclosed herein. Strains sensors disclosed herein can also be used for structural health monitoring (civil engineering, aeronautics), biometrics acquisition (heart rate, motion detection), groundwater contamination testing, in-vivo biochemical analysis (optical fiber catheterization), and drug discovery (new drug screening, cardiotoxicity studies).

In one aspect, a method for fabricating a composite film structure, the method includes determining a desired morphology for a metallic layer of the composite film structure, selecting a first metal substrate based on the determining, transferring a graphene layer on the first metal substrate, depositing the metallic layer on the graphene layer to achieve the desired morphology, and removing the first metal substrate from the graphene and the deposited metallic layer to form the composite film structure. A surface energy difference between the first metal substrate and the deposited metallic layer results in the desired morphology of the metallic layer.

Implementations can include one or more of the following features. The desired morphology can include nanoislands. A distance between edges of nanoislands in the metallic layer can be on the order of molecular dimensions. Depositing the metallic layer can include deposition of evaporated flux of metallic atoms. The evaporated flux of metallic atoms can self-assemble to yield the desired morphology. The evaporated flux of metallic atoms can be produced by electron beam evaporation, thermal evaporation or sputtering. Transferring the graphene layer on the first metal substrate can include exfoliating the graphene grown on a second metal substrate and placing the graphene layer on the first metal substrate. The graphene can include a single layer of graphene. The graphene can be grown on the second metal substrate using chemical vapor deposition. The first metal substrate can include transition metal. The transition metal can include gold, silver, or nickel.

Implementations can include one or more of the following features. A method of forming a substrate for surface-enhanced Raman scattering, the method can include depositing a graphene layer on a first metal substrate, depositing a plurality of metallic nanoislands on the graphene layer, removing the first metal substrate from the graphene and the deposited plurality of metallic nanoislands to form the substrate for surface-enhanced Raman scattering. A method of performing surface-enhanced Raman scattering of an analyte, can include forming a substrate for surface-enhanced Raman scattering, transferring the substrate on an optical fiber, coating the analyte on the substrate; and recording surface-enhanced Raman scattering signals from the analyte. The plurality of metallic nanoislands can include a plasmonically active metal. The plasmatically active metal can include copper, silver, palladium, gold, or platinum nanoislands.

In another aspect, a method of fabricating a thin-film strain sensor, the method includes depositing a graphene layer on a first metal substrate, depositing a metallic layer on the graphene layer, applying a polymer on the graphene layer and the metallic layer; and etching the first metal substrate to form a strain sensor capable of detecting strain spanning four orders of magnitude.

Implementations can include one or more of the following features. The metallic layer can include palladium, the first metal substrate comprises copper and the polymer comprises polydimethylsiloxane.

In another aspect, a method of detecting mechanical movements in a sample, the method includes contacting the sample with a composite film structure, and using the composite film structure to measure electrical signals caused by the mechanical movements. The composite film structure includes a metallic layer deposited on a graphene layer, and a polymer layer on the graphene layer and the metallic layer.

Implementations can include one or more of the following features. The sample can include an airplane component and the mechanical movements can include flexing of the airplane component. Detecting mechanical movements can include detecting cracks in a structure. The sample can include a biological sample and the composite film structure is used external to a body. The biological sample can include an organ, the organ having an interface with ambient air. The mechanical movements can convey physiological information. The physiological information can include one or more of heartrate, pulse pressure, muscle movements, breathing. The body is a portion of a human body, the portion of the human body having an interface with ambient air. The mechanical movements can convey physiological information. The physiological information can include one or more of heart rate, pulse pressure, muscle movements, and breathing. The composite film structure can be part of a wearable sensor to a skin or a clothing. The wearable sensor can be used for in haptic applications. The wearable sensor can be used in instrumented prostheses.

The composite film structure can be used in applications external to a human body. The composite film structure can be used in healthcare applications.

The graphene layer can be deposited on a first metal substrate before a metallic layer is deposited on the graphene layer, and the polymer can be applied on the graphene layer and the metallic layer.

The method can further include etching the first metal substrate prior to contacting the sample with the composite film structure.

Contacting the sample with the composite film structure can include coating the sample with the composite film structure by transferring the composite film structure onto the sample.

The sample includes biological cells. The biological cells include one or more of cardiomyocytes, neurons, muscle cells, and epidermal cells. The metallic layer includes gold nanoislands and the polymer includes polymethylmethacrylate.

In another aspect, a substrate, the substrate includes a layer of graphene, a plurality of metallic nanoislands on the graphene layer, a distance between edges of nanoislands in the plurality of nanoislands being on the order of molecular dimensions. The substrate can be configured for surface-enhanced Raman scattering.

Implementations can include one or more of the following features. The graphene includes a single layer of graphene and the plurality of metallic nanoislands includes gold nanoislands.

In another aspect, a strain sensor, the strain sensor includes a graphene layer, a metallic layer on the graphene layer; and a polymer on the graphene layer and the metallic layer. The piezoresistance of the strain sensor can allow strain spanning four orders of magnitude to be detected.

Implementations can include one or more of the following features. The metallic layer can include palladium, the first metal substrate can include copper and the polymer can include polydimethylsiloxane. The graphene layer can be configured to suppress crack propagation through the metallic layer. A gauge factor at 1% strain of the strain sensor can be at least 1300.

In another aspect, a method of detecting mechanical movements in a biological sample, the method includes coating the biological sample with a composite film structure by transferring the composite film structure onto the biological sample. The method includes using the composite film structure to measure electrical signals caused by the mechanical movements. The composite film structure includes a metallic layer deposited on a graphene layer, and a polymer layer on the graphene layer and the metallic layer, and the biological sample includes engineered, cultured, or harvested cells or tissues, and/or an internal organ.

Implementations can include one or more of the following features. The biological sample includes cultured cells and the cultured cells include one or more of cardiomyocytes, neurons, muscle cells, and epidermal cells. The biological sample includes cultured tissues. The cultured tissues include muscle cells. The biological sample includes an internal organ. The internal organ includes the heart. The graphene layer is deposited on a first metal substrate before a metallic layer is deposited on the graphene layer. The polymer is applied on the graphene layer and the metallic layer. The method includes etching the first metal substrate prior to coating the biological sample with the composite film structure. The first metal substrate includes a transition metal. The metallic layer includes gold nanoislands and the polymer includes polymethylmethacrylate.

In another aspect, a system for measuring mechanical movements in a biological sample, the system includes a chamber, a composite film structure on which a biological sample is disposed, the composite film structure having a metallic layer in contact with a graphene layer, and a polymer layer in contact with either the metallic layer or the graphene layer. The system includes electrical connections for electrically accessing the composite film structure. The system includes a central opening in the chamber, the central opening configured to receive the biological sample disposed on the composite film structure. The biological sample includes cultured cells or tissues. The metallic layer includes a plurality of metallic nanoislands.

Implementations can include one or more of the following features. The polymer layer is in contact with the metallic layer and the biological sample is grown directly on the graphene layer. The polymer layer is in contact with the graphene layer and the biological sample is grown directly on the metallic layer. The polymer layer includes a transparent polymer. The transparent polymer includes one or more of polydimethylsiloxane (PDMS), polymethyl methacrylate (PMMA), and parylene. The layer of graphene includes a single-layer graphene and the cultured cells include cardiomyocytes cultured on the substrate. The plurality of metallic nanoislands includes a plasmonically active metal. The plasmonically active metal includes gold nanoislands, and the electrical connections include electrodes. The composite film structure is configured to generate an electrical signal based on strain due to contractile activities of the cultured cells. The system includes a second pair of substrates configured to sandwich the composite film structure bearing the cultured cells. The composite film structure is configured to generate a signal having a signal-to-noise ratio of more than 40. The composite film structure exhibits a sub-millisecond response time. The system is configured to provide an amplitude and temporal profile of the mechanical movements of the cultured cells. The system is configured to provide an electrical impedance profile associated with an activity of the cultured cells. The system includes a plurality of electrodes, wherein a first electrode is located on one side of the cultured cells, and a second electrode is located on an opposite of the cultured cells. The system further includes an amplifier capable of recording fast current-voltage signals in a time-resolved manner. The system is configured to provide the cellular membrane potential profile due to an activity of the cultured cells. The system is configured to provide a profile of cellular contractility by an optical observation of a change in distance between metallic nanoislands in the plurality of metallic nanoislands. The change in the distance between metallic nanoislands is configured to change a wavelength of optical light used for the optical observation. The system is configured to provide dark-field microscopy data. The system is configured to provide Raman scattering data from the cultured cells.

The details of one or more embodiments of the invention are set forth in the accompanying drawings and the description below. Other features, objects, and advantages of the invention will be apparent from the description and drawings, and from the claims.

Notice the reconstruction on the grain boundary between the merged islands and point defect migrations.

Figure 14:
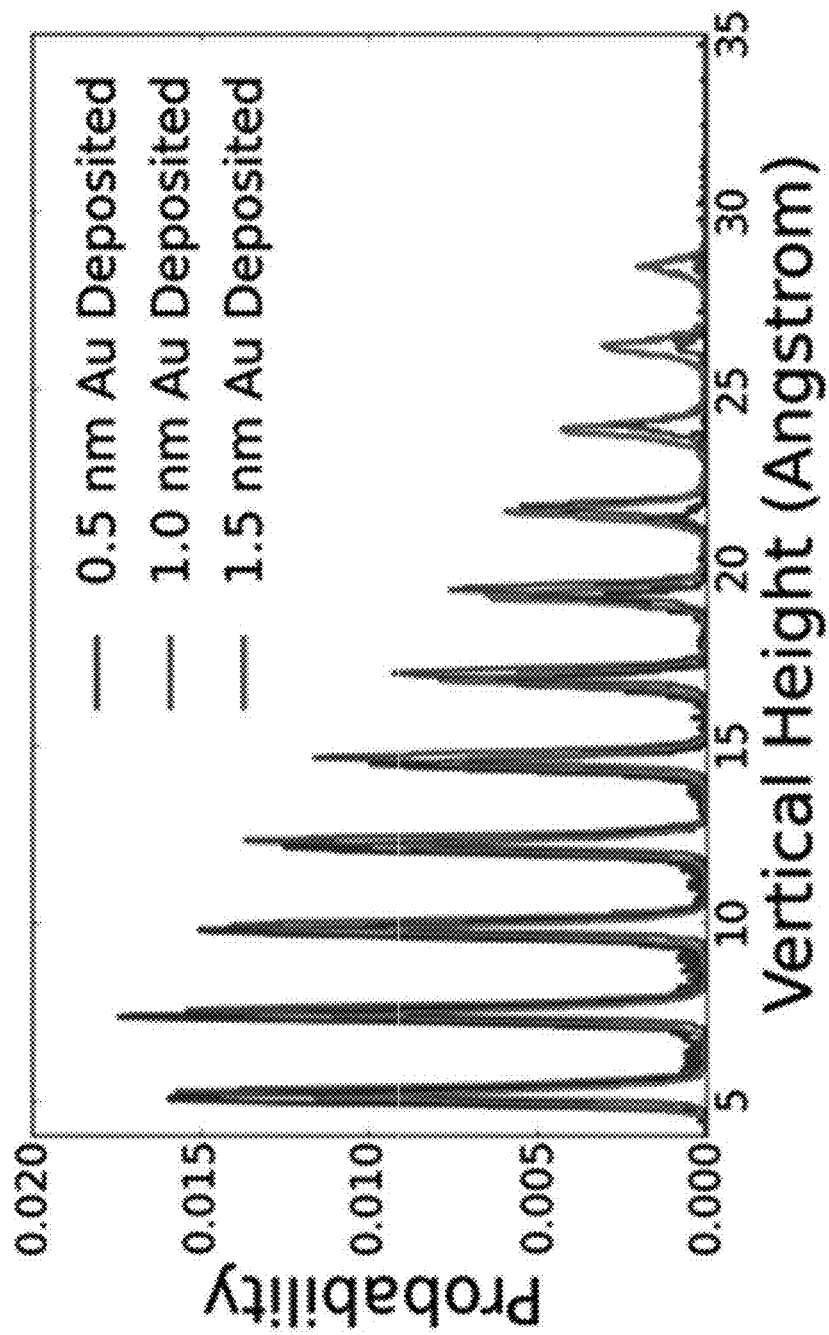

FIG. 14| Monitoring AuNI height distribution during deposition. Simulated distribution of heights of AuNI (graphene and gold) during the deposition of 2 monolayers of gold.

Figure 15:
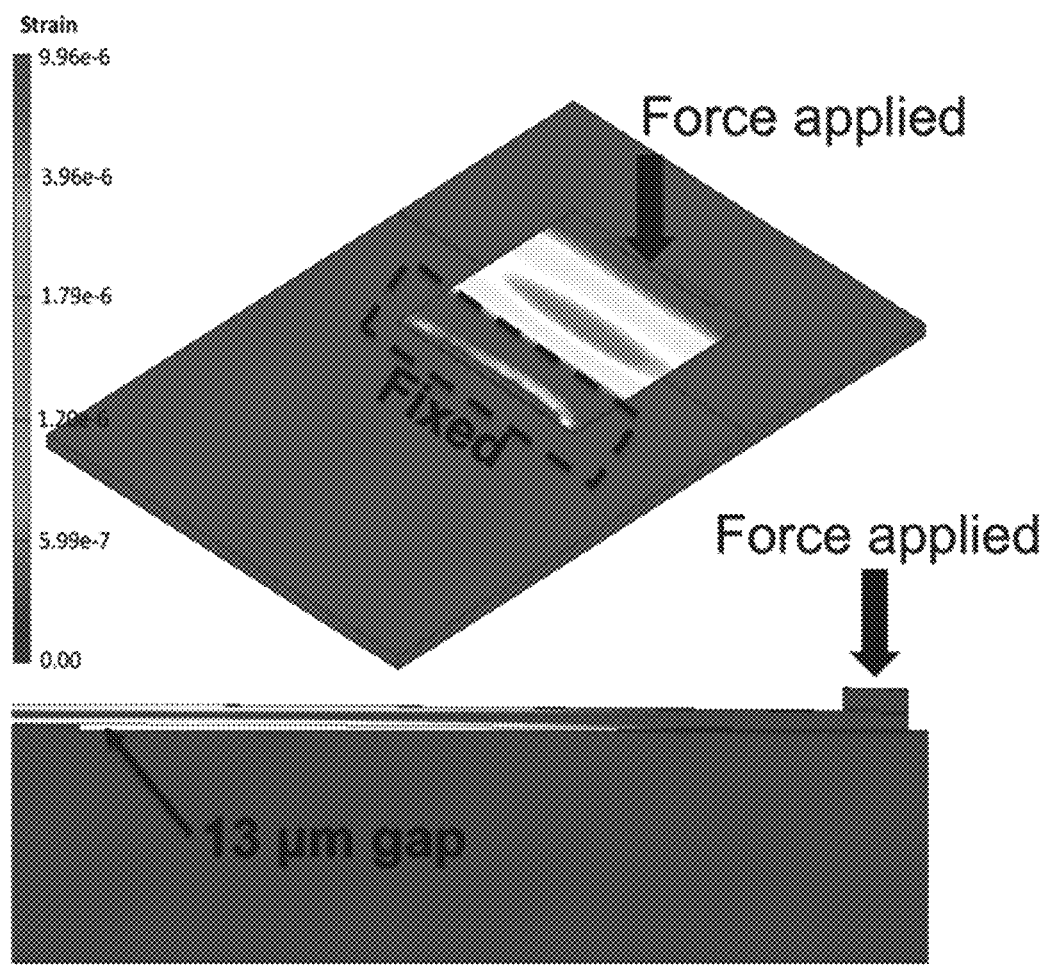

FIG. 15| FEA of glass under small strain. Finite element analysis simulation of the equivalent strain on the glass cantilever bearing graphene/PdNI strain sensor after applying 0.1N force to the edge of the cantilever. The fop surface of the cantilever experiences the maximal tensile strain of 0.001%

Figure 16:
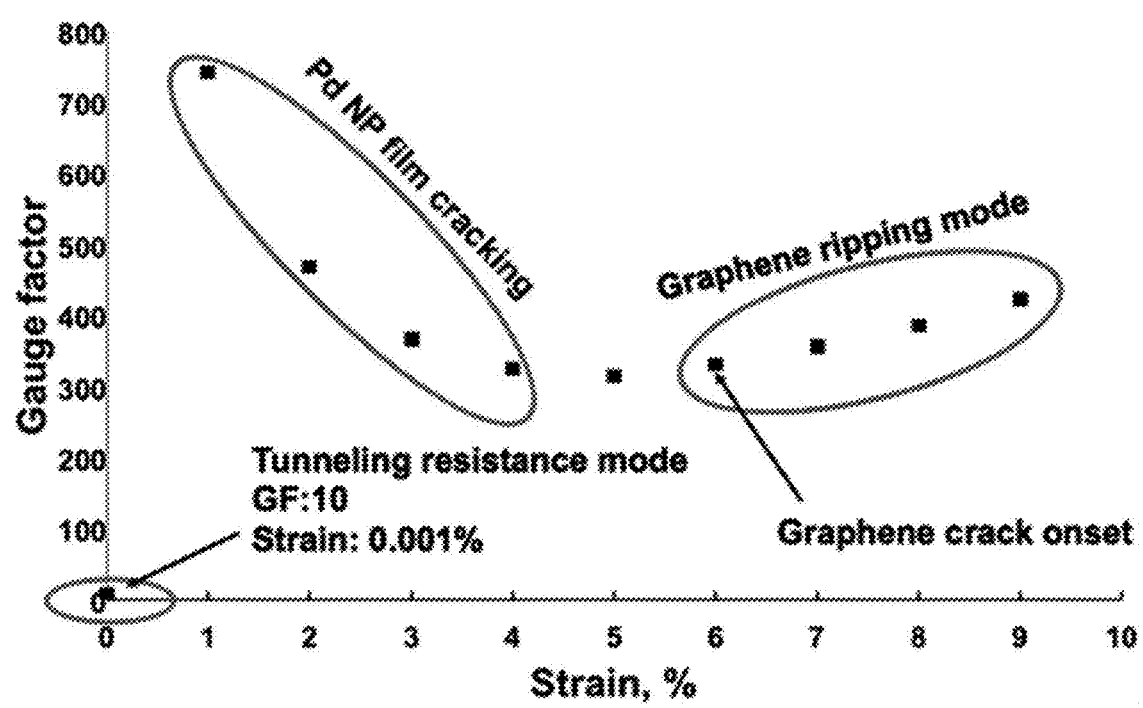

FIG. 16| Three sensing modes of graphene/PdNI sensors. The plot of the gauge factor versus strain % for graphene/PdNI strain sensors indicates three major sensing modes: interparticle tunneling resistance modulation (<<1% strain), PdNI film cracking (<6% strain), and graphene cracking (>6% strain). Note that the lowest value for 0.001% strain was obtained by flexing 130 μm-thick glass slides bearing graphene/PdNI films (FIG. 22a), while the rest of the values were obtained with sensors transferred to PDMS strips (FIG. 22b).

Figure 17:
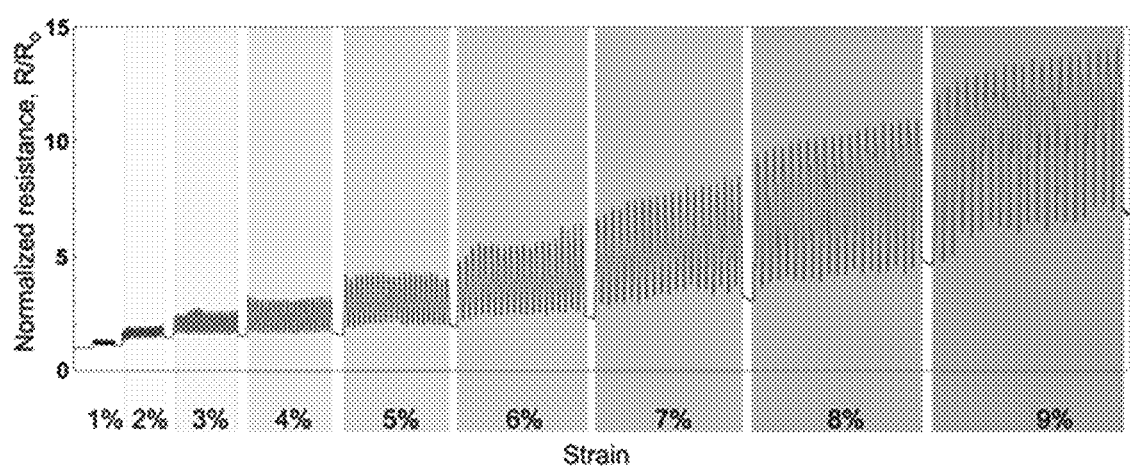

FIG. 17| Graphene as strain sensor. Normalized resistance plot of graphene on PDMS stretched cyclically (20 cycles for each strain) to 1, 2, 3, . . . 9% strain. Notice that the baseline within a set of 20 strain cycles is stable until 6% strain is reached (graphene crack onset). The step-wise baseline shift between the sets of different cycles is due to the viscoelastic response of the PDMS substrate.

Figure 18:
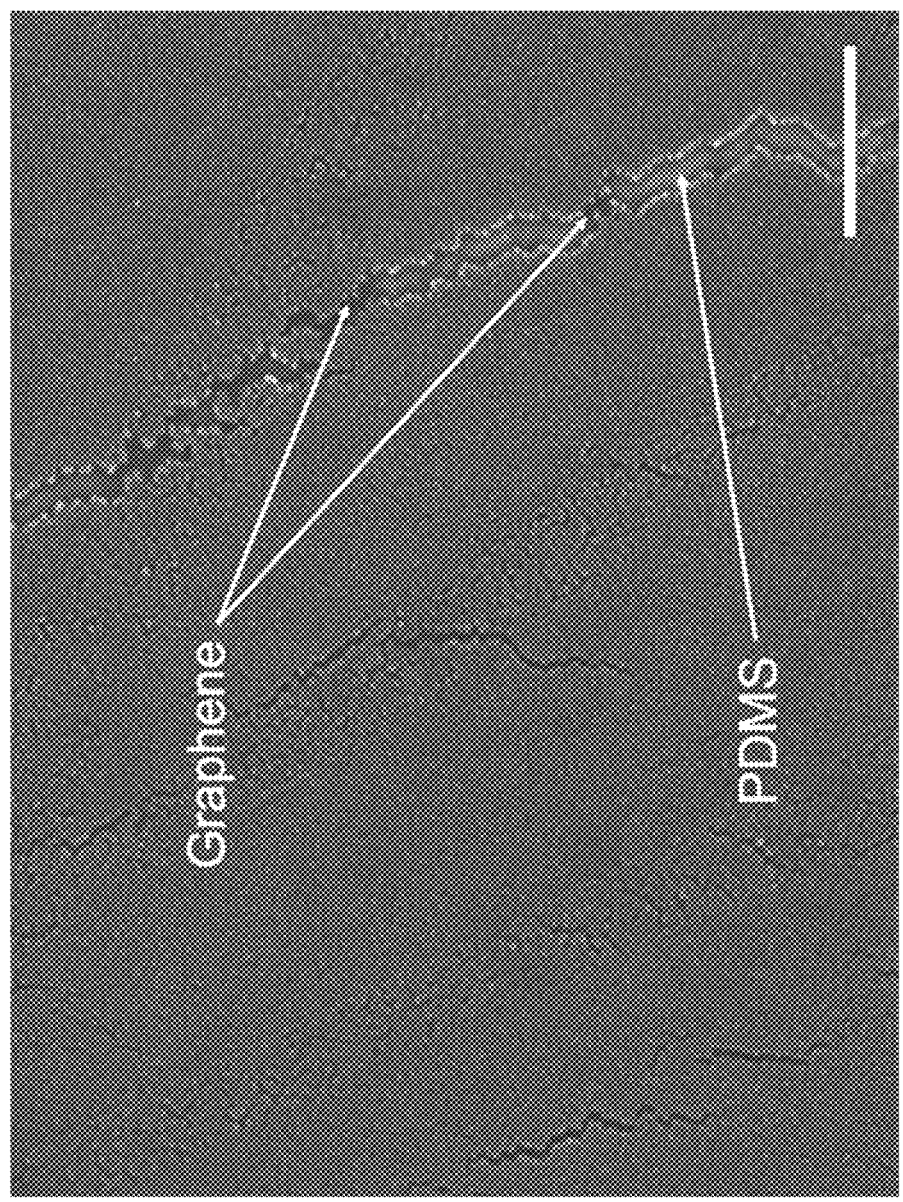

FIG. 18| Graphene/PdNI sensor under 5% strain. Scanning electron micrograph of the PDMS/graphene/PdNI strain sensor under tensile strain of ~5% (h). Scale bar: 200 nm.

Figure 19:
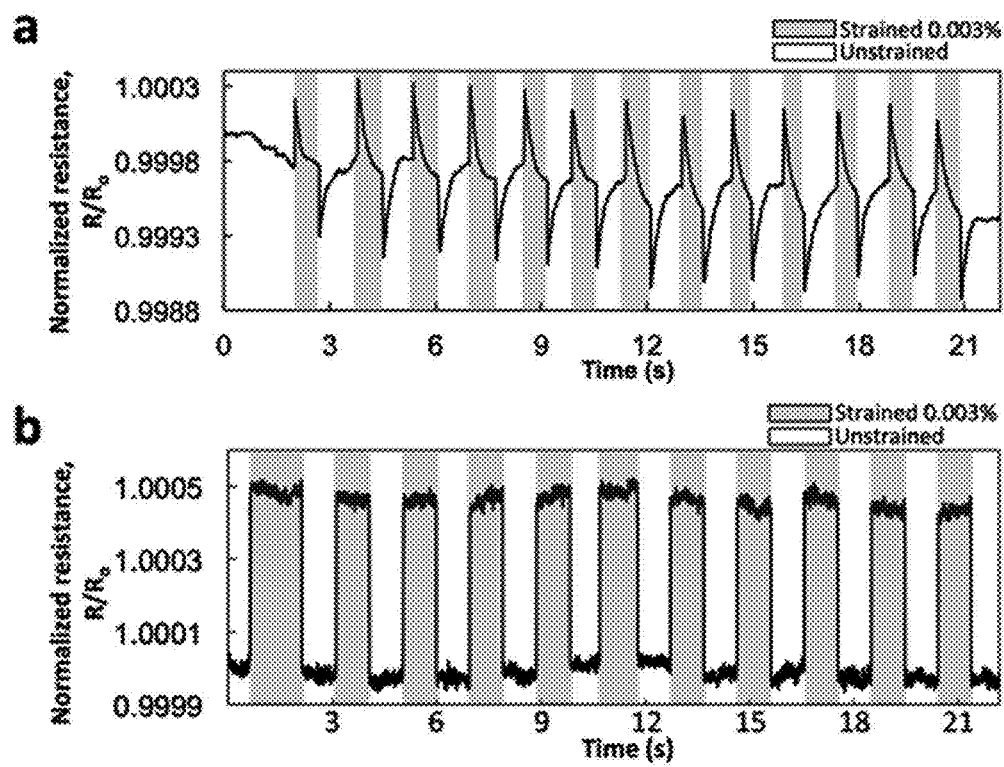

FIG. 19| Solid Pd thin film sensor vs. graphene/PdNI sensor. Normalized resistance plots of solid (100 nm) film Pd strain sensor on glass coverslip under cyclic tensile strain of 0.003% (a) and the graphene/PdNI strain sensor on glass coverslip under cyclic tensile strain of 0.003% (b). Notice that at similar gauge factors (~17) at 0.003%, the PdNI sensor demonstrates stable behavior (holds the resistance value during the one second strain cycle), while the solid Pd film sensor registers the applied strain but does not hold the resistance value and reverts the it back to the baseline (upon returning the sensor into unstrained position, the resistance value drops and then reverts to the baseline during the one second unstrained cycle). This observation suggests that at very small strains (<<1%), the grain boundaries in the solid Pd film reconstruct to minimize the separation between the grains, which makes impossible to register static strains with such sensors. Conversely, PdNI sensors demonstrate good stability for static strain measurement.

Figure 20:
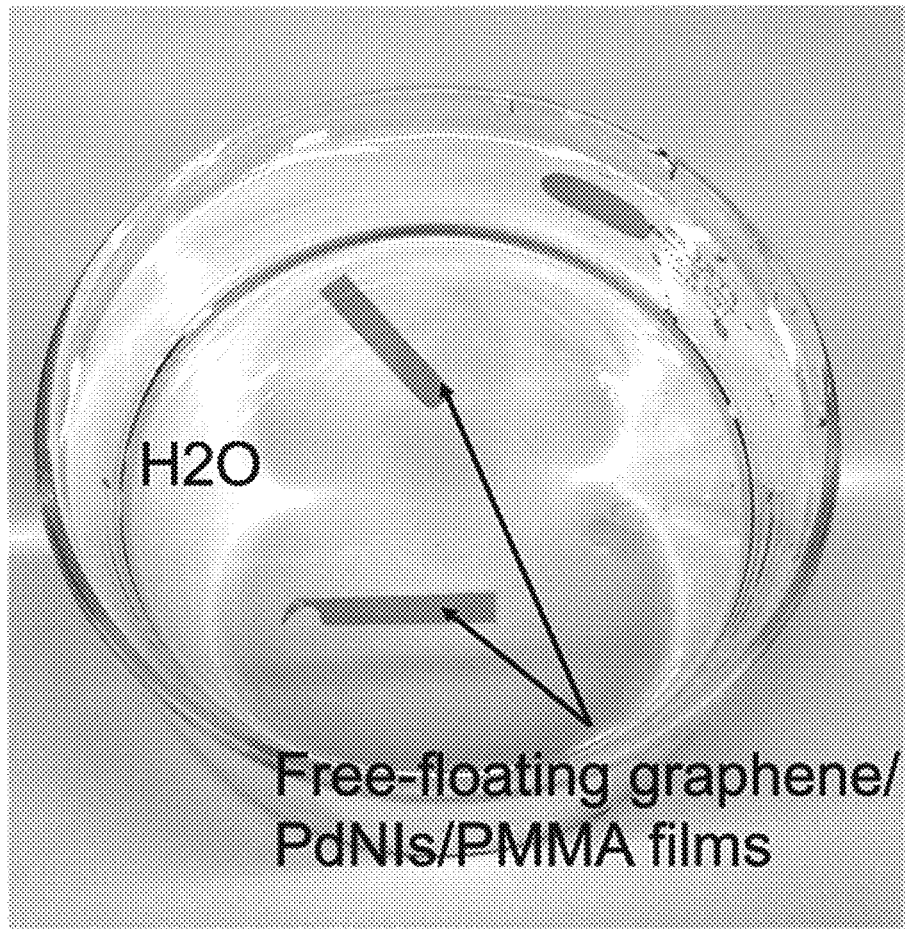

FIG. 20| Free-floating graphene/NI films. A photograph of free-floating graphene/PdNI/PMMA films after copper etching and transferred into a DI water bath.

Figure 21:
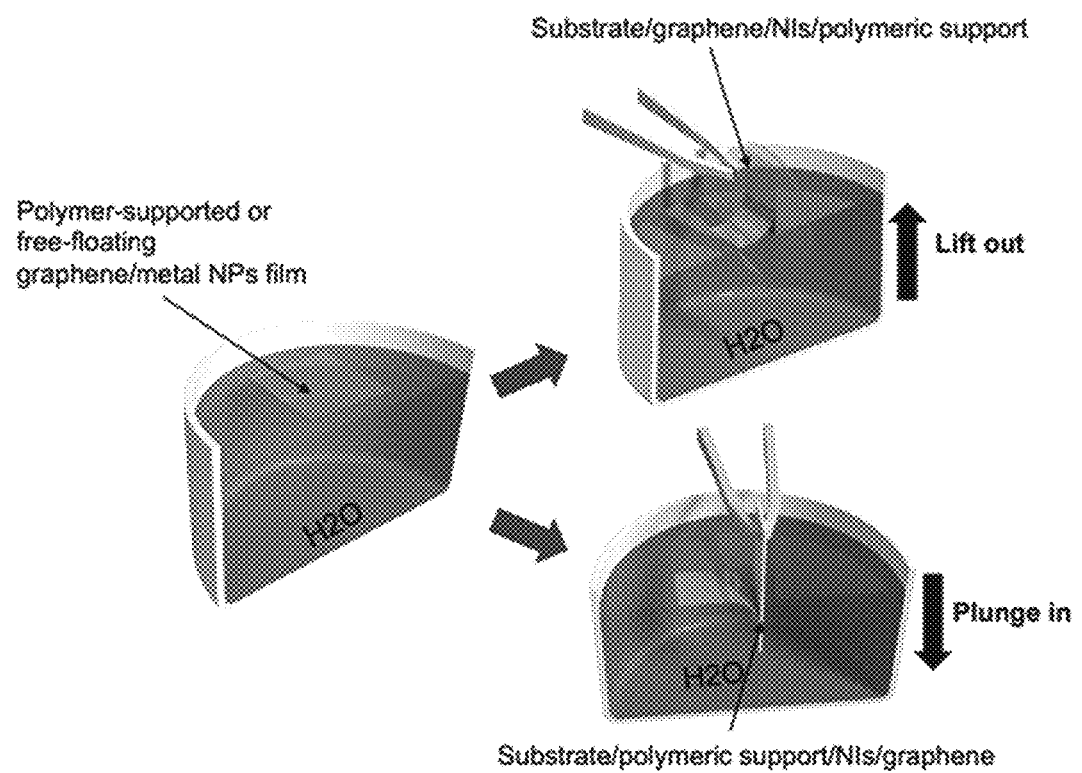

FIG. 21| Graphene/NI transfer. Rendered schematic of depositing free-floating graphene/NI/polymeric support (or no polymer) onto the final receiving substrate.

Figure 22:
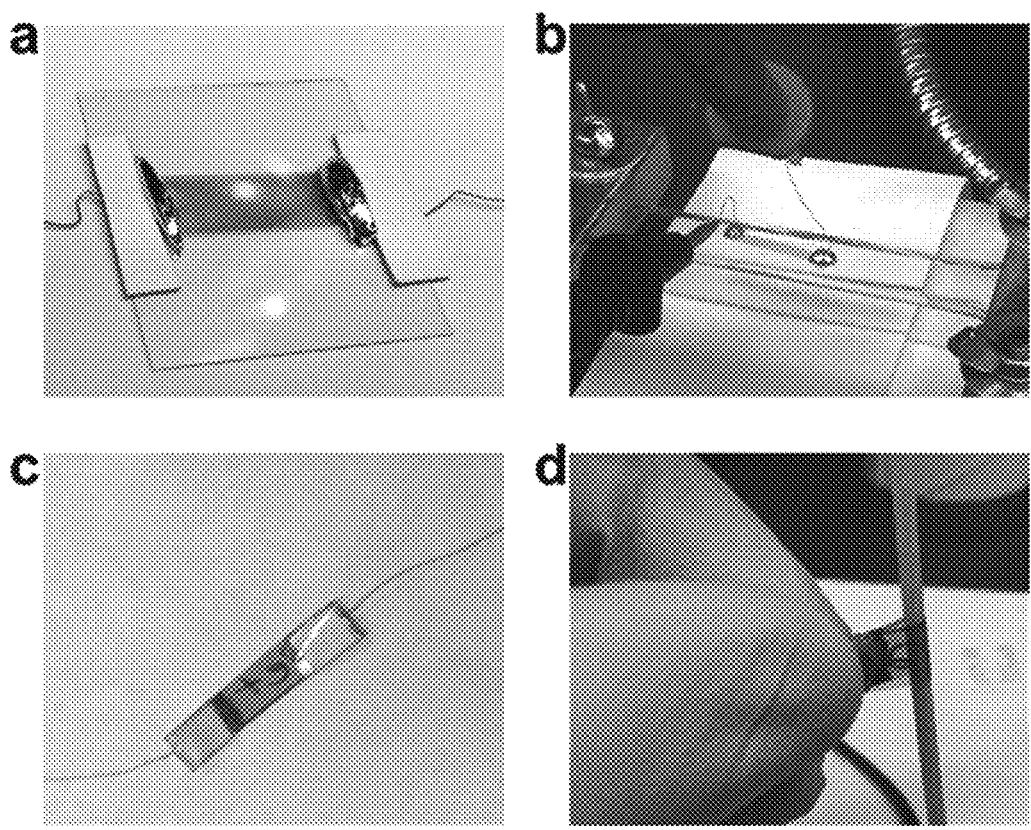

FIG. 22| Graphene/PdNI sensors of rigid, flexible, and stretchable substrates. Optical photographs of a graphene/PdNI film transferred onto a glass coverslip and electrically addressed with EGaIN and copper wires (a), graphene/PdNI film transferred onto a strip of PDMS under tensile strain cyclic loading (b), PET/PdNI/graphene strain sensors unstrained (c) and bent around a toothpick (d) under ~1% tensile strain.

Figure 23:
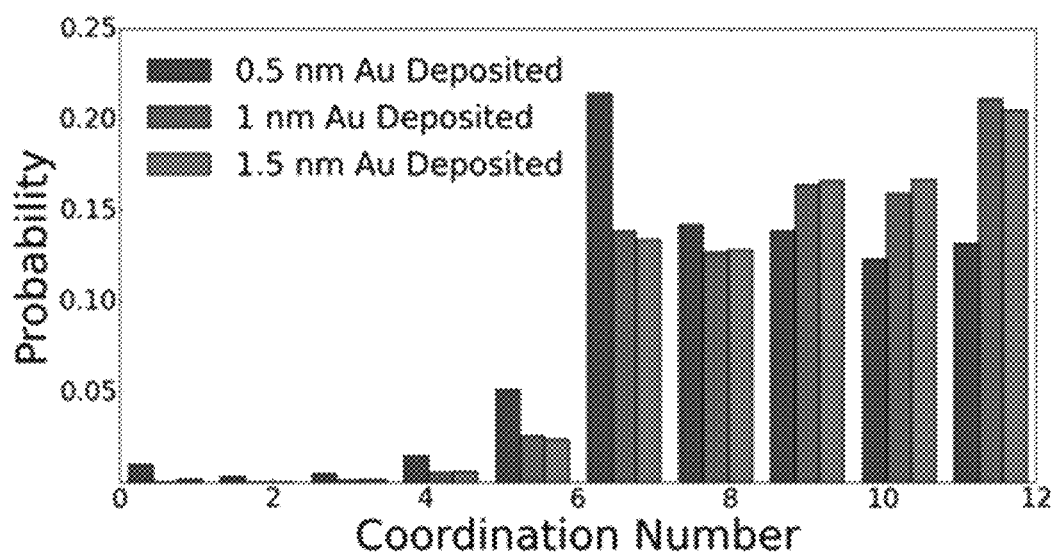

FIG. 23| Evolution of the coordination number probability distribution as the gold islands are deposited.

Figure 24:
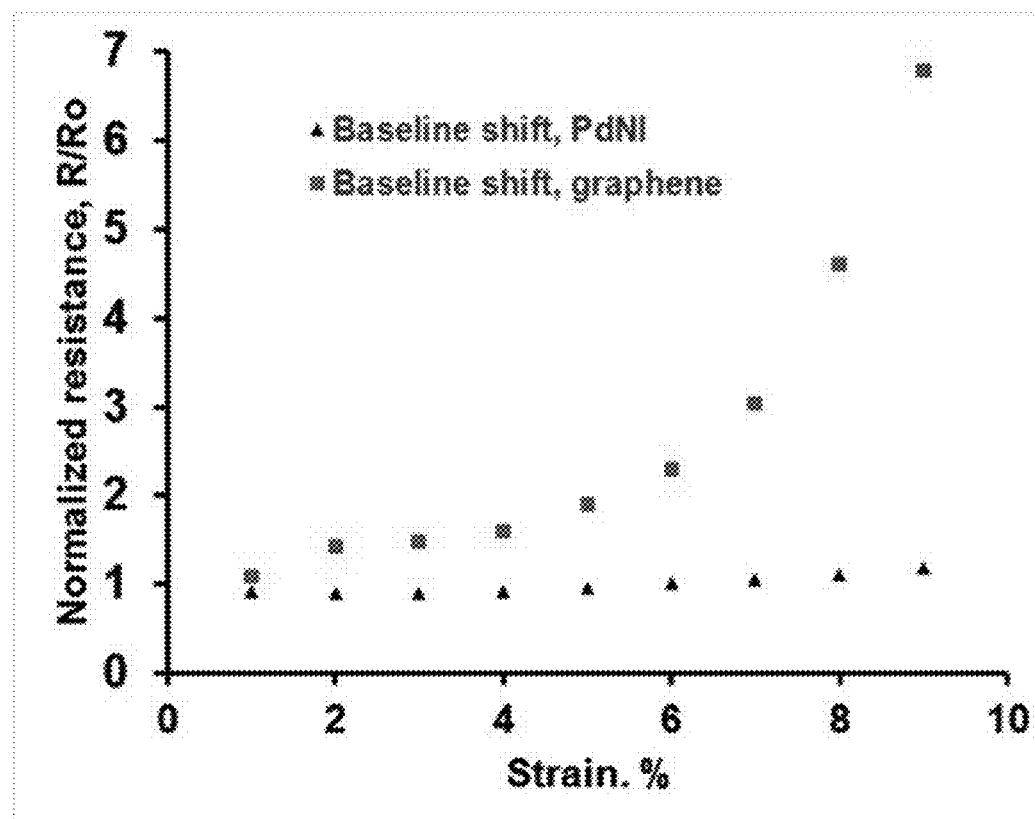

FIG. 24| Sensor baseline stability. Plot of the baseline shift (normalized resistance) after 1% strain increments (20 cycles per increment) for PdNI sensor on PDMS (black triangles) and graphene on PDMS (squares). Notice the stability of the PdNI sensor (the baseline normalized resistance drops by 0.11 until 3-4% strain is reached, potentially due to Pd particle repacking; after which it rises minimally to 1.18 after 9% strain cycles). The baseline of the graphene control was rising steadily until 5-6% was reached (graphene crack onset), after which the baseline rose exponentially and reached 6.80 after 9% strain cycles. This indicates that cracks in PdNI films can effectively reclose thus ensuring the stability of the sensor at high strains.

Figure 25:
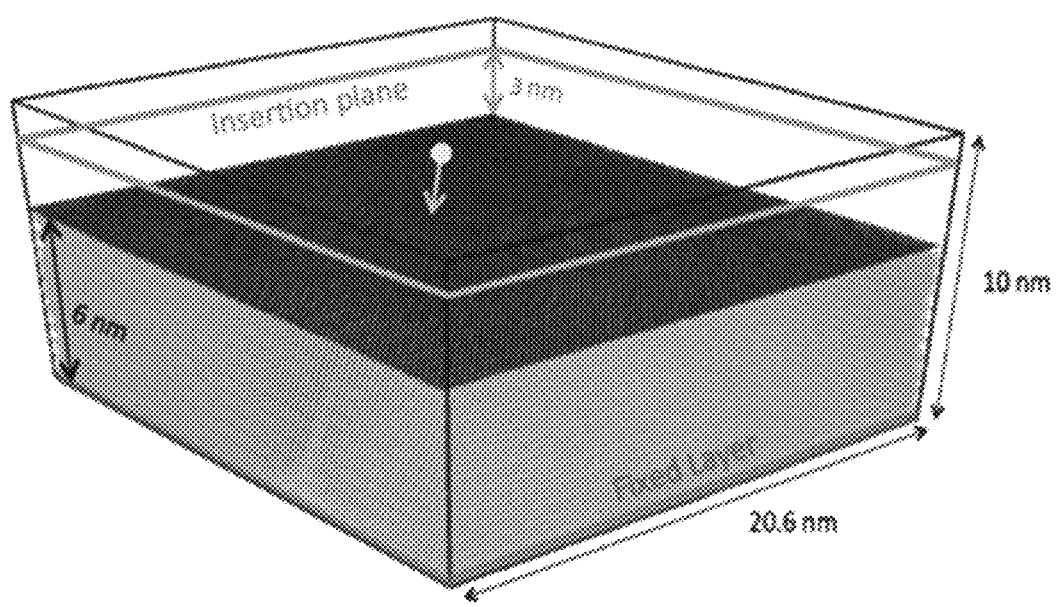

FIG. 25| Simulation box. Schematic showing the geometry of the graphene/copper substrate.

Like reference symbols in the various drawings indicate like elements.

DETAILED DESCRIPTION

Physical vapor deposition (PVD) of metallic thin films can be used in manufacturing and research. It can be understood as a process of physical self-assembly. That is, an evaporated flux of metallic atoms produced within the deposition chamber in PVD can become a thin film deposited on a substrate, and the structure of the thin film is a complex function of the metal and substrate, along with the pressure, temperature, and rate of deposition. At low nominal thicknesses (e.g., <50 nm) on typical substrates such as glass, polymeric films, single crystalline substrates such as silicon, boron nitride, and silicon carbide, etc., the morphology most often produced is disconnected islands. In general, islands are regions of films that are isolated. This morphology is generally not regarded as being compatible with thin-film electronics. There are, however, applications that can exploit various characteristics of these islands, provided that the islands could be generated reproducibly and on a support that would permit facile transfer to any other surface.

The wetting transparency of graphene (i.e., the adoption of the surface energy of its underlying substrate by graphene) allows the morphology of a thin metallic film (e.g., ≤20 nm, ≤10 nm) deposited on graphene by evaporation to vary based on the identity of the substrate supporting the graphene. For example, the morphology can depend strongly on the substrate supporting the graphene.

In this way, graphene allows control of the formation of a range of geometries: tightly packed nanospheres, well faceted nanocrystals, and island-like formations with controllable gaps down to 3 nm, or on the order of molecular dimensions such as between ~2 Å to a few nanometers. Tightly packed can refer to a monolayer of nanoparticles having a maximized number of immediate neighbors. Nanospheres are a type of nanoislands that adopted a spheroidal shape.

These graphene-supported structures can be transferred to any surface and function as substrates for surface-enhanced Raman scattering (SERS) (e.g., including on the tips of optical fibers) and ultra-sensitive mechanical signal transducers with an wide useful range (e.g., at least four orders of magnitude of strain) for applications in structural health monitoring, electronic skin, and measurement of contractions in cells, such as cardiomyocytes. These composite film structures of metal and graphene can thus be treated as a platform technology for multimodal sensing.

Structural health monitoring can include strain measurement and the monitoring of crack propagation through bridges, building foundations, airplane wings and turbine blades, etc. Electronic skin refers to epidermal sensors that are wearable on skin and have mechanical properties similar to skin mechanical properties). These sensors can sense touch, temperature, and proximity, for example.

Moreover, they are low profile, for example at or below 20 nm in thickness, mechanically robust, semitransparent, and have the potential for reproducible manufacturing over large areas. Being semitransparent cam also these sensors to be placed on a window pane, fighter jet heads-up display (HUD). Semitransparency also allows imaging of cells (or other samples) through the sensor under a microscope.

Graphene has several attractive characteristics when incorporated into functional nanocomposite thin film structures. It is flexible (and stretchable—compared to metallic films—to strains of 5-6%), conductive, transparent, amenable to large-area growth and transfer to many substrates, and its crystalline grains can extend over dimensions reaching 1 cm.

Graphene is the thinnest obtainable 2D material that can produce wetting transparency. Wetting transparency was previously explored primarily with respect to liquids, where quantities such as contact angle can depend strongly on the surface energy of the layer or substrate supporting the graphene.

Figure 1:
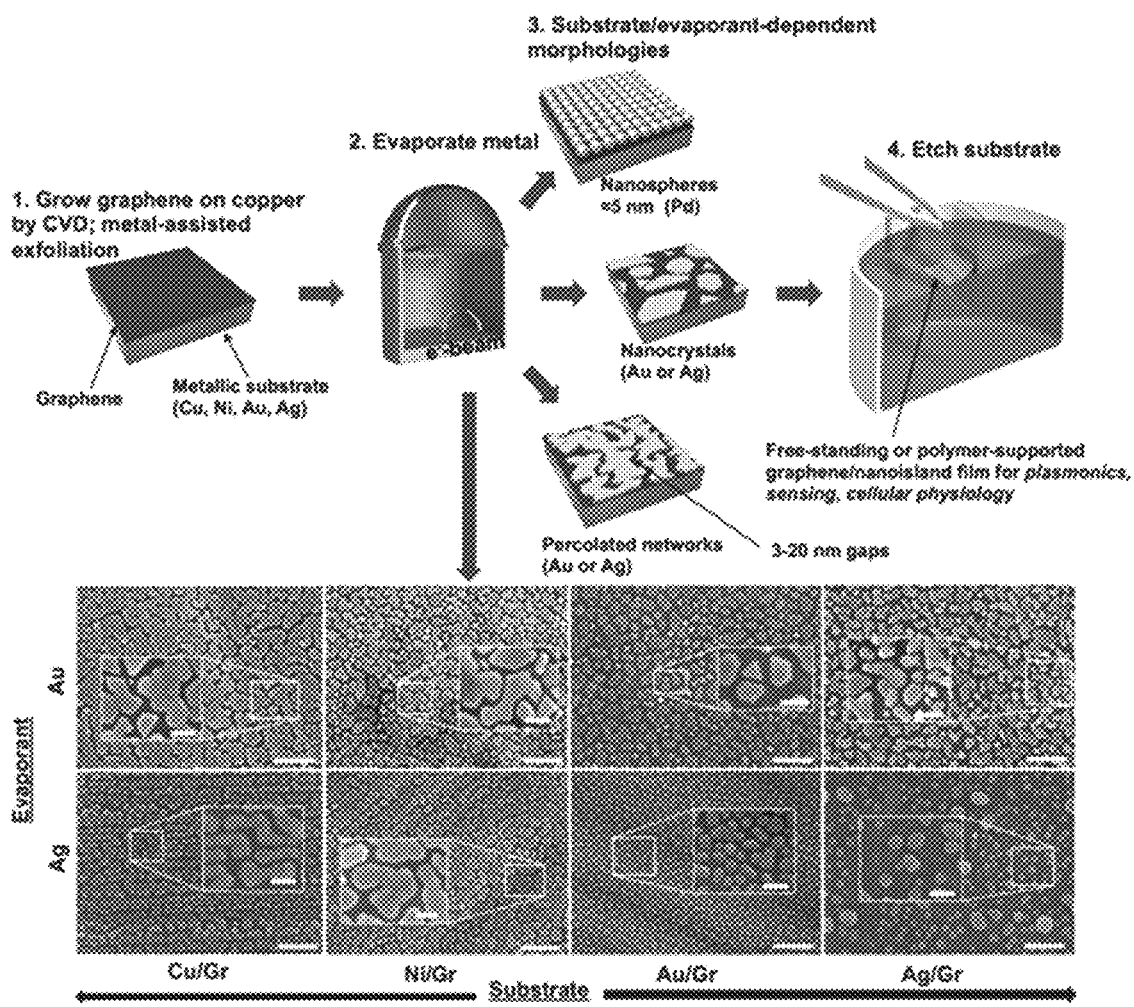
FIG. 1| Schematic diagram of the process used to generate nanoislands (NI) (top) and scanning electron micrographs of metallic nanoislands on various substrates obtained by electron beam evaporation of evaporant (y-axis) onto a graphene/metal substrate (x-axis) (bottom). 10 nm of gold (first row) and 10 nm of silver (second row) evaporated onto (left to right): graphene on copper foil (as grown), MAE-transferred graphene on nickel, MAE-transferred graphene on gold, MAE-transferred graphene on silver. Each evaporant was deposited onto the substrates concurrently in the same chamber. Scale bars: 200 nm. Scale bars in insets: 50 nm.

The systems and methods disclosed herein demonstrate that this concept extends to an evaporated flux of atoms. A metal/graphene bilayer or metal/graphene composite film structure can serve as a template for the self-assembly of nanoparticles of diverse and controllable morphologies—nanospheres, nanocrystals, and percolated networks—by electron beam (e-beam) evaporation. FIG. 1 illustrates this concept and the range of morphologies available when only the evaporated metal (gold and silver) and the substrate were changed (copper, nickel, gold, and silver), keeping all other parameters constant. These graphene/nanoisland (NI) films exhibited sufficient robustness to transfer to nearly any surface. The films are also characterized by sharp tips and gaps (i.e., distance between edges of the nanoislands) approaching molecular dimensions that make them amenable to sensing of chemical, optical, and mechanical stimuli.

Figure 5:
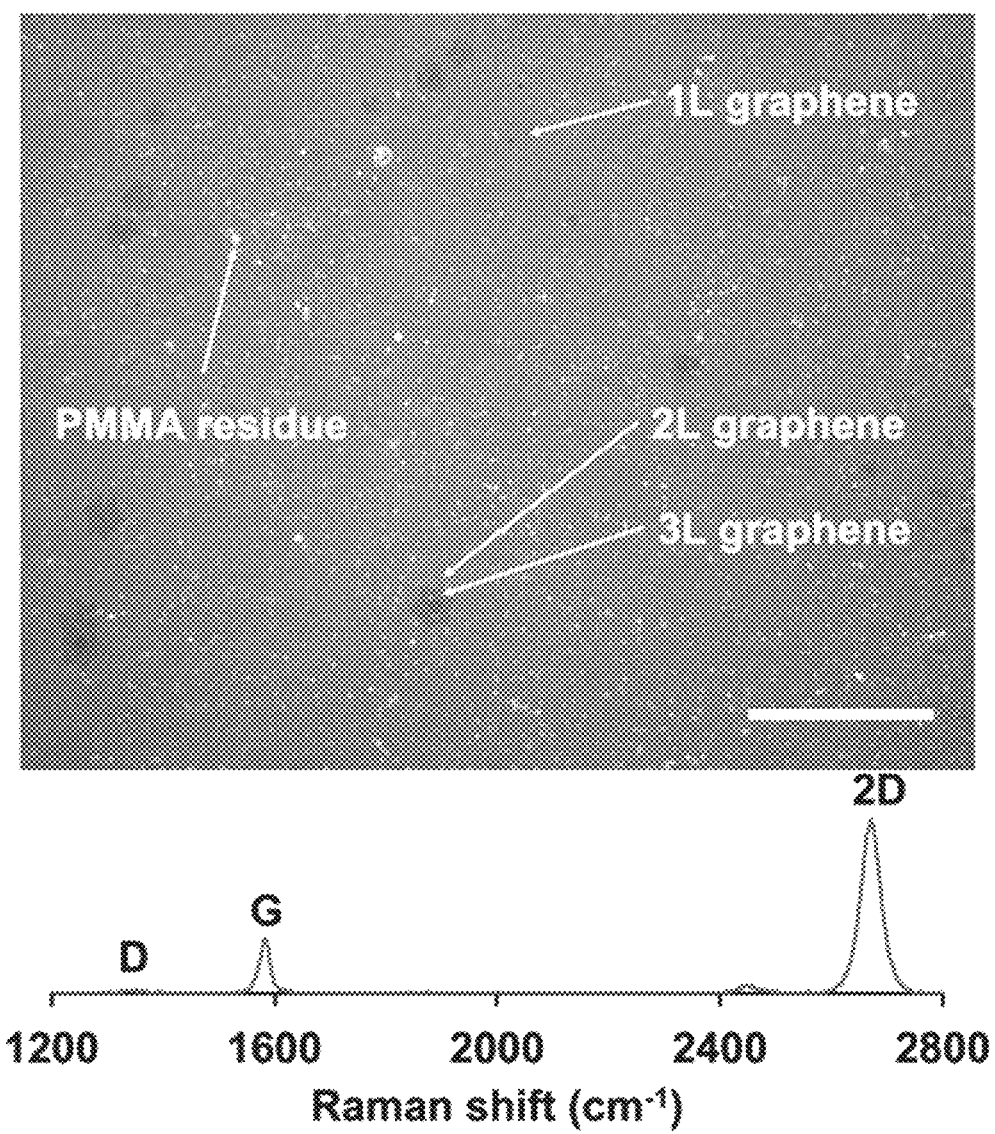
FIG. 5| Single-layer graphene. Optical micrograph of single layer CVD graphene wet-transferred to a silicon wafer with 90 nm thermal oxide (top). Scale bar: 100 µm. RAMAN spectrum of single layer CVD graphene wet-transferred to a silicon wafer with 90 nm thermal oxide (bottom). The ratio of the prominent graphene peaks indicate high-quality, predominantly single-layer graphene (D/G ratio: 0.019. 2D/G ratio: 3.1).

The nanoislands can be self-assembled on single-layer graphene synthesized on copper foils by chemical vapor deposition (CVD), as shown in FIG. 5. To transfer graphene from copper onto other metals (gold, silver, and nickel), metal-assisted exfoliation (MAE) can be used.

In a single concurrent deposition of thin (e.g., 10 nm) metal films (e.g., gold, silver, or palladium) onto graphene on various substrates (e.g., copper, nickel, gold, and silver) the apparent crystallinity, shape and size distribution of the resulting nanoislands, extent of percolation, as well as the size of the gaps between the islands can be different for each substrate. The extent of percolation is the amount of connectedness between the islands.

Figure 6:
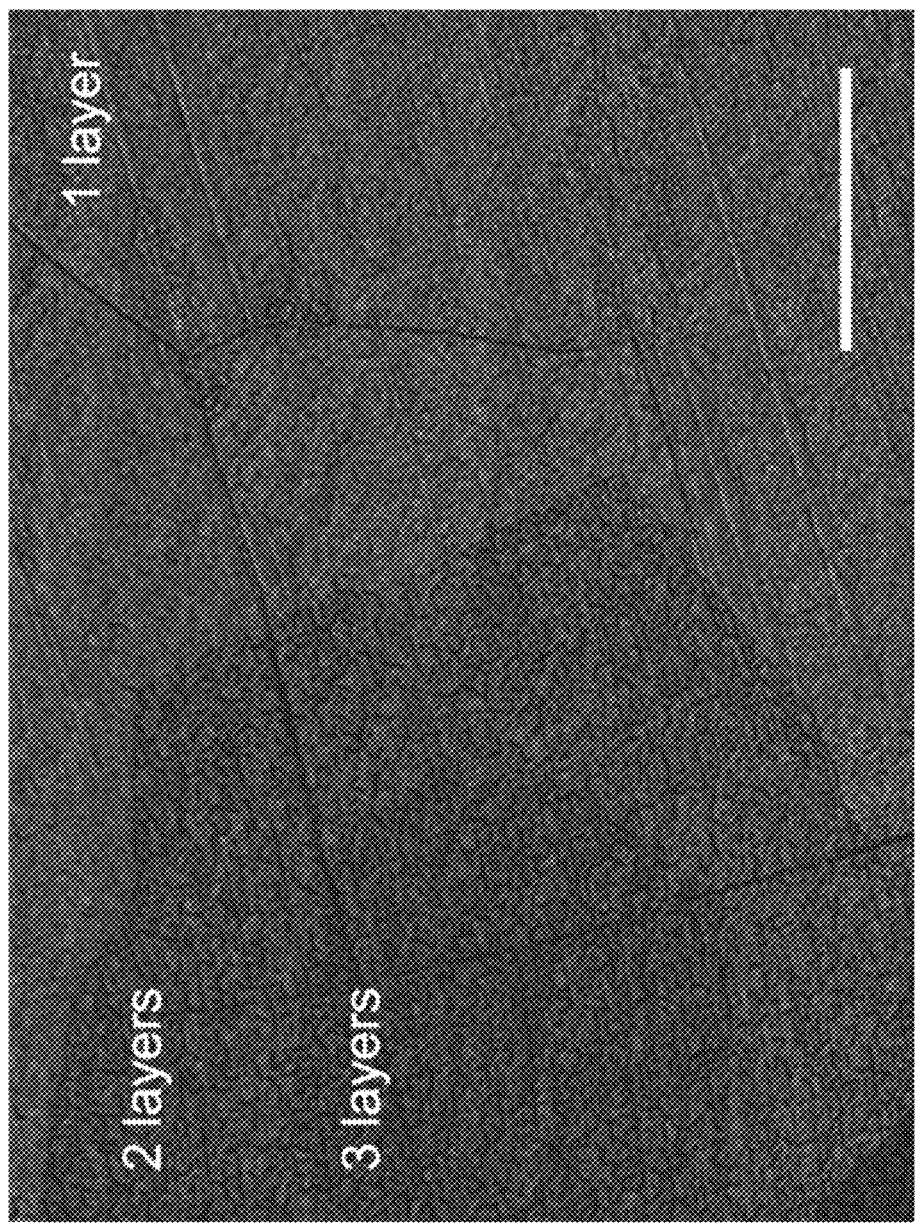
FIG. 6| NI on different substrate grain orientations. Scanning electron micrograph of AgNI (10 nm deposition) on graphene on copper. Scale bar: 1 µm. Notice the copper grain boundary diagonally across the image (from bottom left to top right) and the difference in AgNI morphology (percolation, level of anisotropy) on the respective copper grains.
Figure 7:
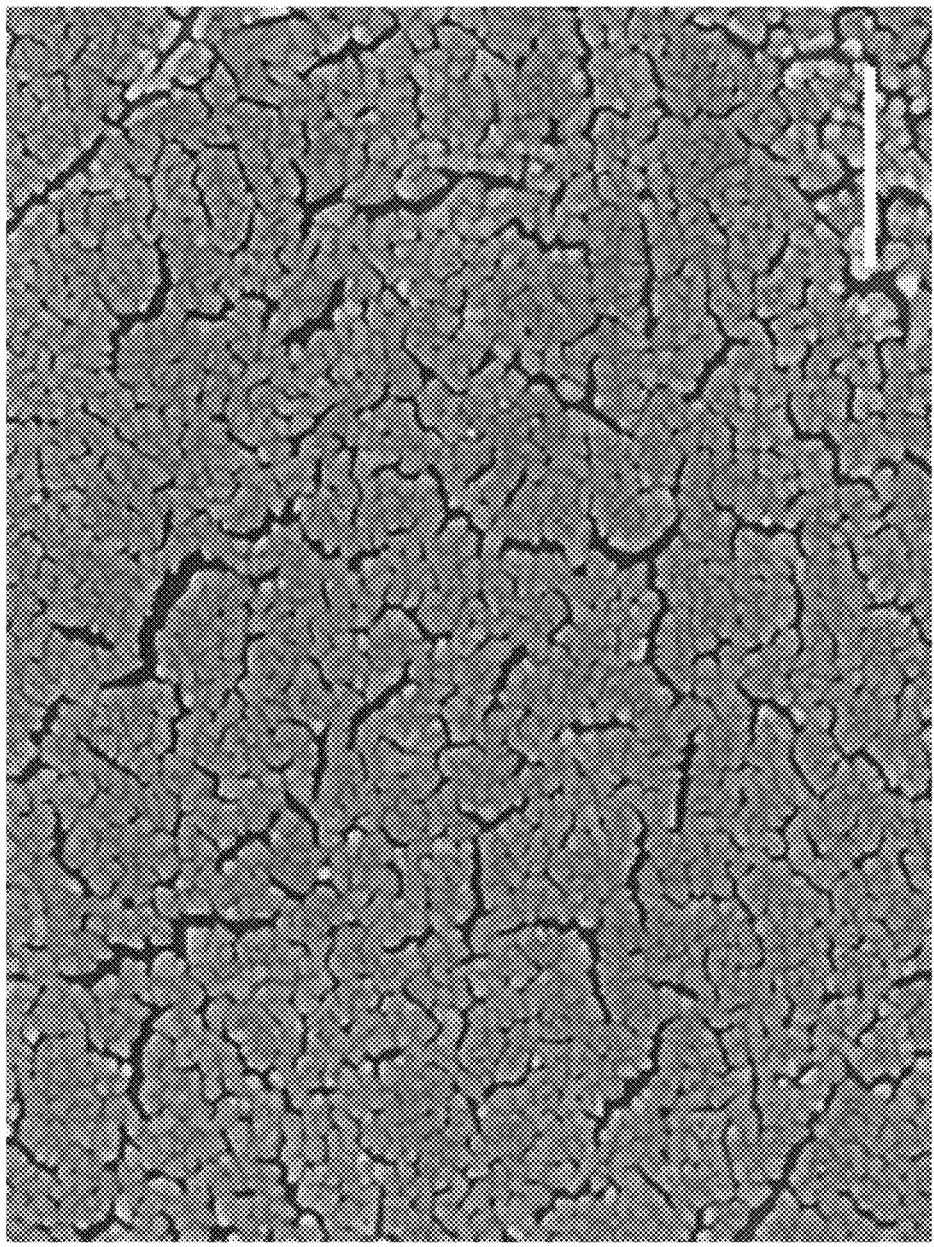
FIG. 7| NI on multiple layers of graphene. Scanning electron micrograph of AuNI (10 nm deposition onto graphene on copper) on graphene transferred onto Parylene-C (etching copper after deposition of 1 µm-thick film of Parylene C (graphene is on top in this image and is covering the gold islands). Notice the change in the amount of percolation in gold islands deposited over 1, 2, and 3 layers of graphene on copper. Scale bar: 2 µm.
Figure 8:
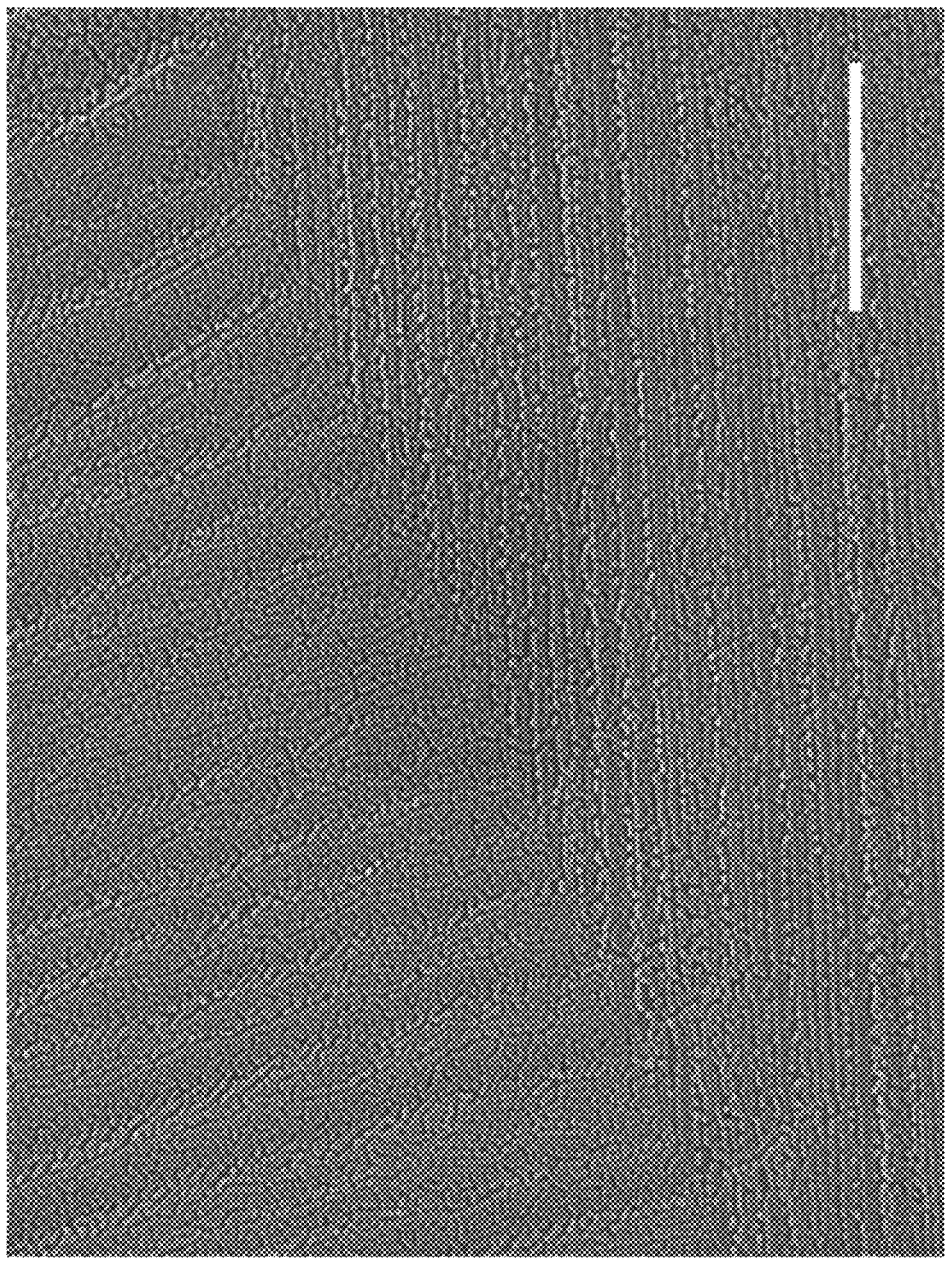
FIG. 8| NI deposited at high evaporation rate. Scanning electron micrograph of AuNI (10 nm deposition) on graphene on copper deposited at the rate of 2 Å/s. Compared to the slow rate of deposition (0.1 Å/s, FIG. 1, bottom) the structure of the gold islands demonstrates significantly higher granularity, complete percolation, and significantly higher area coverage. Scale bar: 200 nm.
Figure 9:
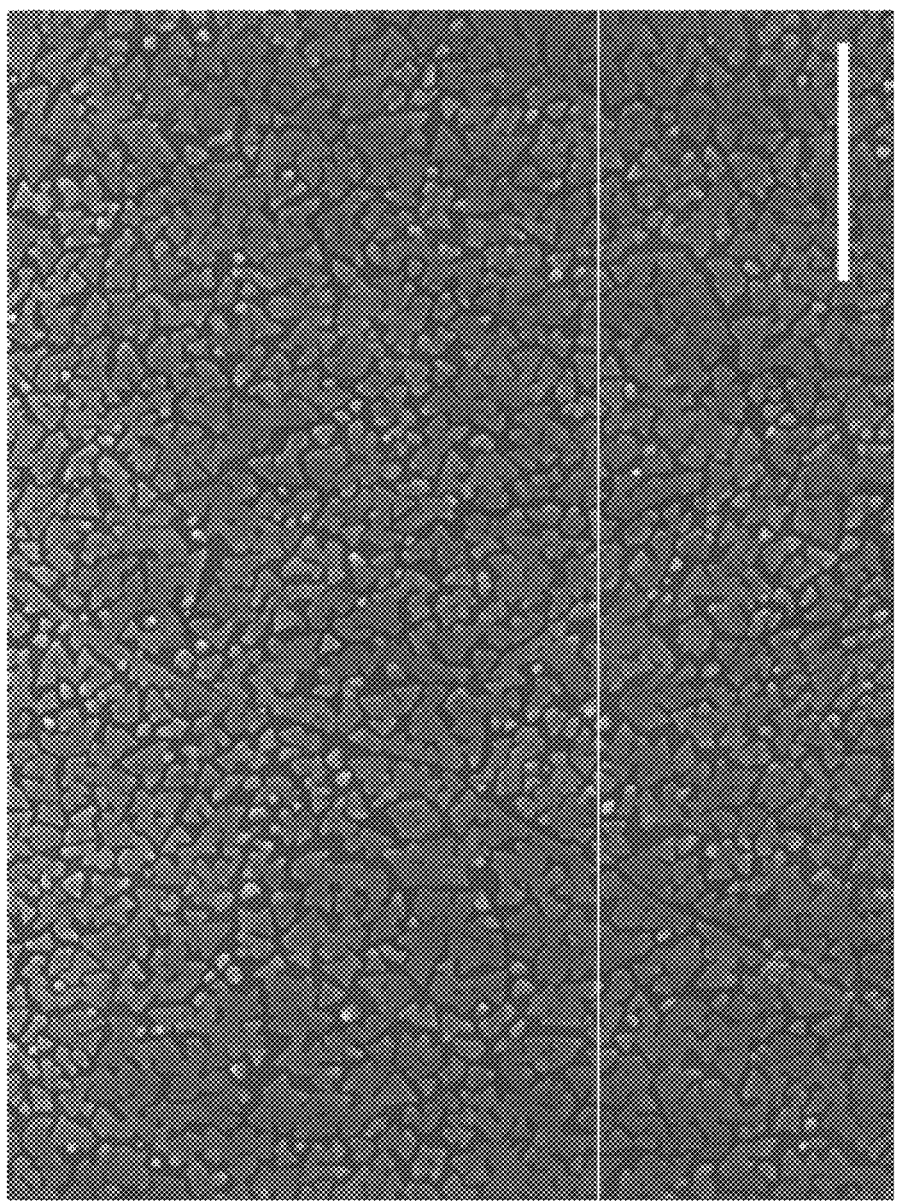
FIG. 9| NI deposited at elevated temperature. Scanning electron micrograph of AuNI (8 nm deposition) on graphene on copper deposited at the rate of 0.1 Å/s and the substrate temperature ~500 K (100 K higher than SDC in FIG. 1).
Figure 10:
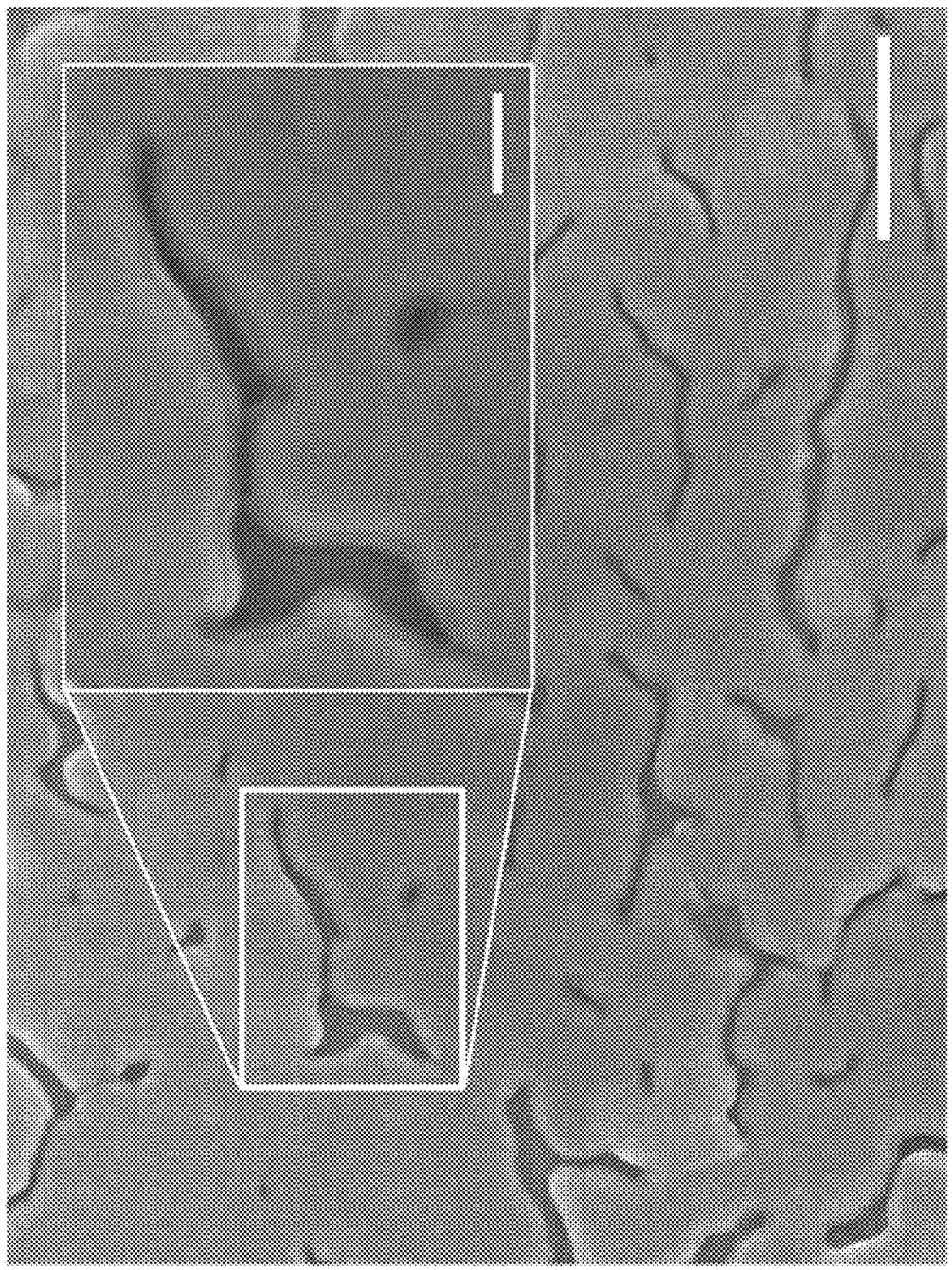
FIG. 10| Thermal annealing of AuNI. Scanning electron micrograph of AuNI (10 nm deposition) on graphene on copper foil after vacuum annealing at 600 K for 1 h. In comparison to the unannealed sample (FIG. 2, top left), notice merging and spreading of the islands. Scale bar: 200 nm. Scale bar in inset: 50 nm.
Figure 11:
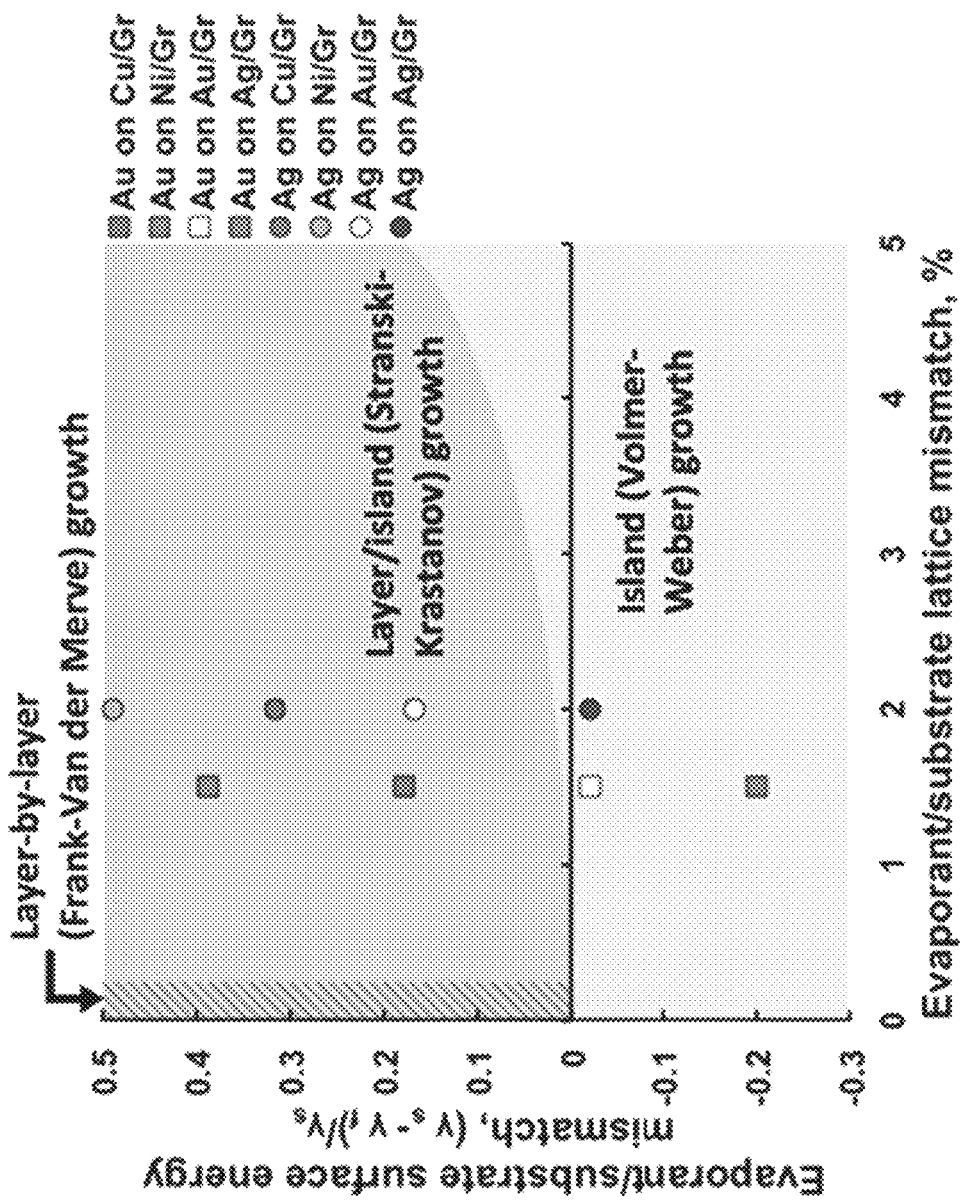
FIG. 11| Wet transfer transforms AuNI. Scanning electron micrograph of AuNI (10 nm deposition) synthesized on graphene on copper foil and transferred onto a glass slide. Scale bar: 200 nm. Scale bar in inset: 50 nm. In comparison to the non-transferred sample (FIG. 1, bottom left), notice merging of the islands into a completely percolated network and smoothing of the crystal facets. The metamorphosis is potentially due to etching of the copper substrate (surface energy 1650 mJ/m$^2$) away and floating the Au island/graphene film on the surface of water (surface energy 72 mJ/m$^2$) during the wet-transfer process. Scale bar: 200 nm. Scale bar in inset: 50 nm.
Figure 12:
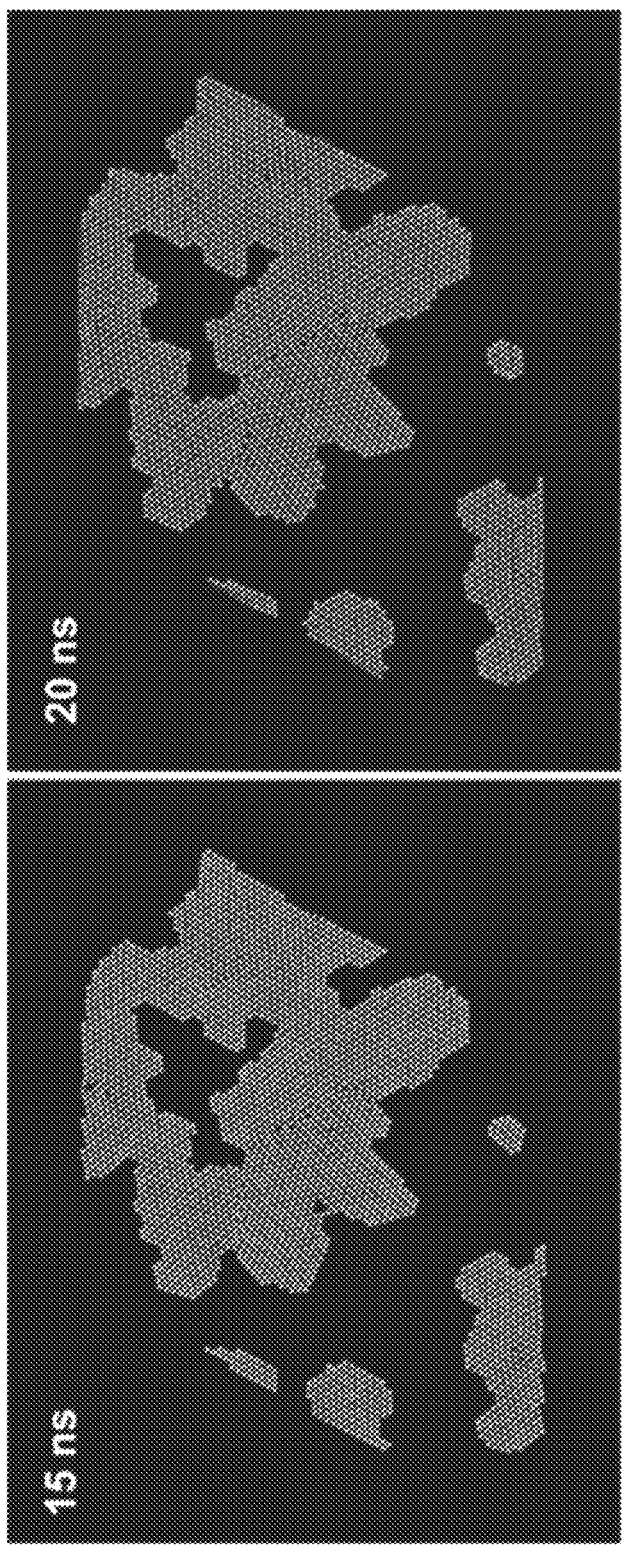
FIG. 12| Thin-film growth model. Plot of the evaporant/substrate surface energy mismatch (vertical axis) vs. evaporant/substrate (graphene) lattice mismatch (horizontal). Stability regions of the three major modes of film growth are indicated on the plot: layer-by layer (cross-hatch), layer/island (gray), island (light gray). Note that due to the wetting transparency of graphene, the surface energy of the substrate was calculated as surface energy of the substrate metal less 2% (hence notice the vertical position of same-evaporant/same-metal substrate (Au on Au/Gr and Ag on Ag/Gr) at −0.02. The substrate lattice constant was taken as that of graphene (2.46 Å) (the effect of the strain (≈0.5%) on graphene by the underlying substrates was negligible and not accounted for). This model does not take into account the Moiré patterns (first-order: substrate/graphene and second order: substrate/graphene/evaporant) that can possibly influence the nanoisland morphology. Notice a good accord of the model with the experimental results (FIG. 1, bottom): higher degree of nanoisland percolation and graphene area coverage suggests the Stranski-Krastanov mode (Cu/Gr, Ni/Gr substrates), while the systems located in the Volmer-Weber stability zone (Ag on Ag/Gr, Au on Ag/Gr, and Au on Au/Gr) clearly have a purely nanoisland morphology.
Figure 13:
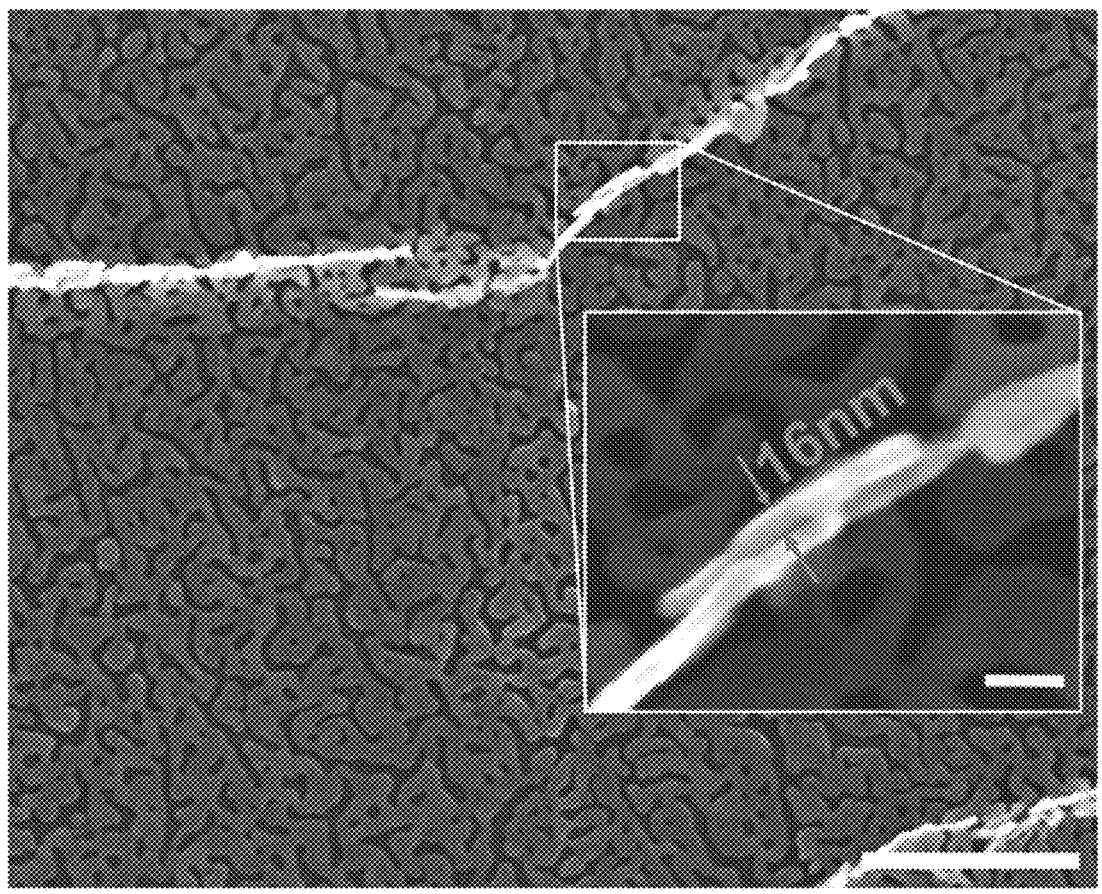
FIG. 13| Monitoring graphene/gold interface events. LAMMPS simulation of thermal annealing (500° K) of gold nanoislands on graphene on copper. Represented is the reconstruction of the bottom layer of gold (in contact with graphene) over a 5 nanosecond-period during annealing.

For example, the resulting morphologies can directly depend on the nature of the substrate material such as its surface energy and crystallographic orientation, as shown in FIG. 6. The resulting morphologies can also depend on characteristics of the evaporated metal, such as its surface energy and lattice mismatch with graphene (as shown at the bottom of FIG. 1), the number of graphene layers (as shown in FIG. S3), as well as processing parameters such as rate (as shown in FIG. S4) and amount of deposition, temperature of the substrate (as shown in FIG. S5), thermal annealing after deposition, (as shown in FIG. S6) and transfer to the final receiving substrate (as shown in FIG. S7).

The strong dependence of the final morphology of the islands on the identity of the metal supporting the graphene suggests growth that may follow rules similar to those developed for epitaxial growth. Generally, three major modes for film growth can exist in a two-element (e.g., evaporant and metal substrate) system: layer-by-layer (Frank-Van der Merve), layer/island (Stranski-Krastanov), and island proper (Volmer-Weber).

These modes are determined largely by the mismatches of the lattice dimensions and the surface energies between the evaporant and the substrate. A larger lattice mismatch favors island growth, while positive surface energy difference, $(\gamma_{substrate}-\gamma_{film})/\gamma_{substrate}$, favors layer-by-layer growth. Inserting graphene between the evaporant and the substrate thus permitted tuning of the surface energy by changing the substrate metal, assuming some degree of wetting transparency of the graphene. The lattice mismatch between the evaporant and the graphene can be essentially fixed (±0.5% of the mismatch value, due to the substrate-induced strain on graphene). The lattice mismatch is the arithmetic difference between the periodic interatomic distance (in the crystalline material) of two materials divided by the periodic interatomic distance of one of them (e.g., the substrate).

Diffusion barrier $(E_d)$ is the amount of energy an adsorbed atom has to overcome in order to move from one lattice site to the neighboring one. The $E_d$ for gold is 0.05±0.01 eV. Considering the very low diffusion barriers for gold and silver on graphene and a low rate of deposition (consistent with thermodynamic—as opposed to kinetic—control), the system with graphene is biased toward island growth mode but still correlates quite well with the model (as shown in FIG. S8). When a first product (e.g., product A) forms faster than a second product (e.g., product B) because the activation energy for product A is lower than that for product B even though product B is more stable, then product A is the product that is favored under kinetic control and product B is the thermodynamic product and is favored under thermodynamic control Massively parallel atomistic simulations of the deposition and annealing of gold atoms onto a graphene-coated copper (111) surface can be performed to elucidate the mechanism of nanoisland formation. Accurate interatomic potentials are available for copper/graphene/gold and experimental fabrication of such an architecture can be accomplished in the least number of steps.

Figure 2:
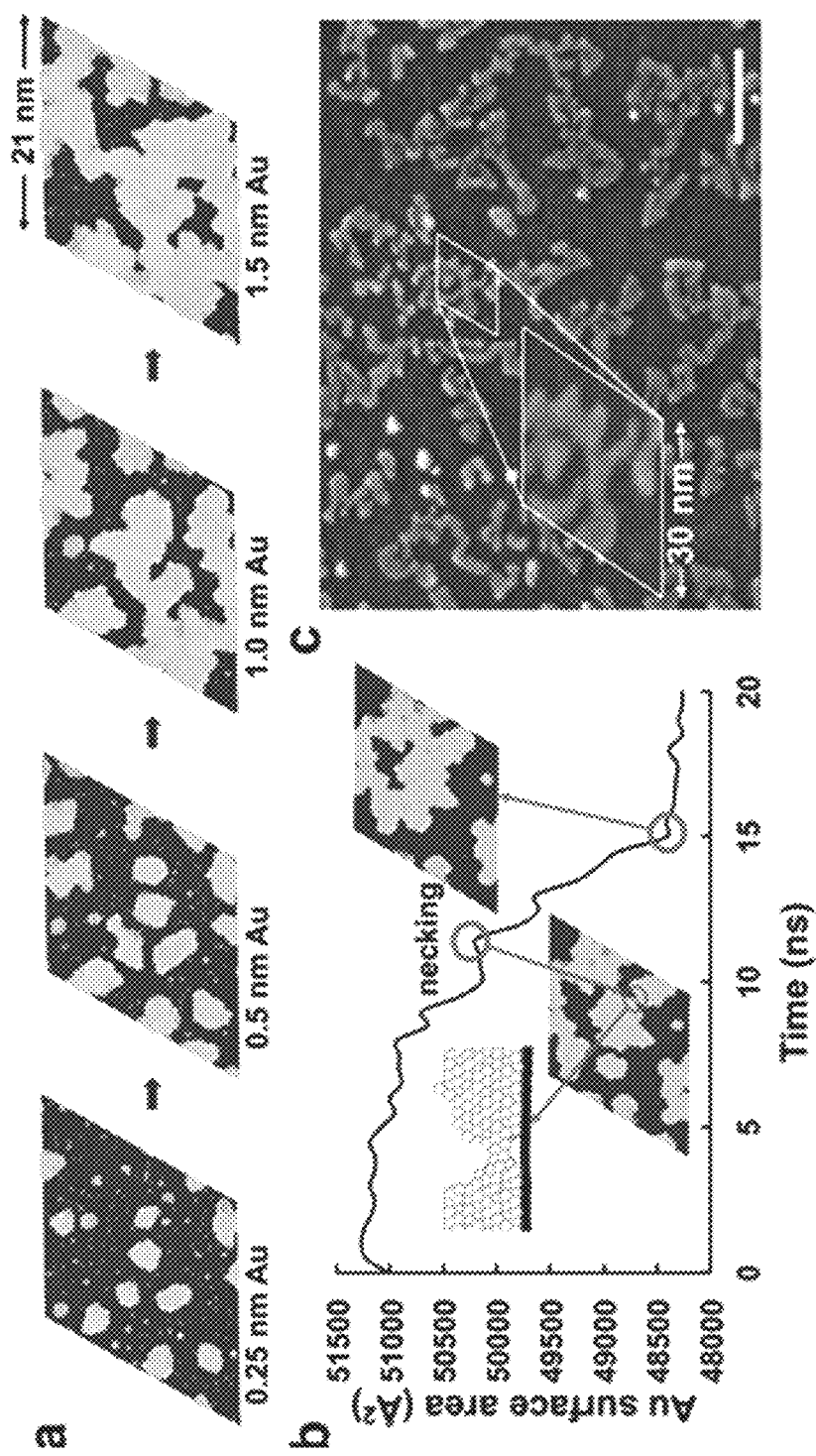
FIG. 2| Microstructural evolution of nanoislands as predicted by molecular dynamics simulations. a, Simulated evaporation of 1.5 nm of gold onto graphene on copper. b, Plot of the change of the total surface area of gold nanoislands during 20 ns of vacuum annealing at 500 K. Merging of nanoislands is preceded by crystallographic alignment and necking (surface area increase). c, Scanning electron micrograph of 1 nm of gold evaporated onto graphene on copper. Scale bar: 50 nm.

The deposition of five monolayers of gold (~30,000 atoms) onto a 3×3 copper/graphene Moiré super cell (~240,000 atoms) over the course of 150 ns at 400 K was studied. The simulated deposition rate was about nine orders of magnitude faster than the experimental rate (30 s per monolayer), producing an initial morphology in the simulated deposition that is kinetically controlled, as shown in FIG. 2a.

A simulation of thermal annealing of the gold nanoislands on graphene on copper (three monolayers of gold deposited) at 500 K for 20 ns was performed to generate a thermodynamically controlled morphology for comparison with experiment. FIG. 2b shows the decrease in the total surface area of gold during the annealing. Merging of islands occurred during the initial 15 ns, as noted by the decrease in the net surface area of gold, after which the rate of change of the island morphology became diminished. This observation suggested that the simulated deposition process indeed generated kinetically trapped clusters that aggregated over short (ns) timescales. The morphology predicted by the simulation in FIGS. 2a and 2b was verified experimentally for the deposition of 1 nm gold in FIG. 2c. The similarity between the simulated and experimental morphologies is striking considering that the experiment was performed after the simulation and that the parameters used in the simulation were not adjusted to fit the experiment.

The ability to predict the morphology and the manipulability of the graphene-supported nanoislands can enable applications in chemical and mechanical sensing.

For example, films of noble metals are widely used as substrates for surface-enhanced Raman scattering (SERS). The large increase of the electric field in the gaps between the metallic nanostructures upon illumination of radiation having a frequency resonant with that of the plasmon frequency, $\omega_p$ enhances Raman scattering and allows label-free identification of molecules in the vicinity of the nanostructures. The plasmon frequency can also be a function of the geometry of the particles, in addition to the material the film is composed of. Nanostructures are provided in the films of noble metals for example by sputtering onto a substrate, self-assembled into a film from solution/air interface, prepared as a Langmuir-Blodgett film, patterned out a solid film, for example.

Placing SERS-active substrates onto optical fibers can allow remote sensing. Remote sensing can involve the sensing of a chemical environment that is physically removed from the analyzing equipment. For example, using a 100 ft. optical fiber to sense water contamination due to fracking 100 ft. deep underground in real time without the need to extract samples for the analysis.

Figure 3:
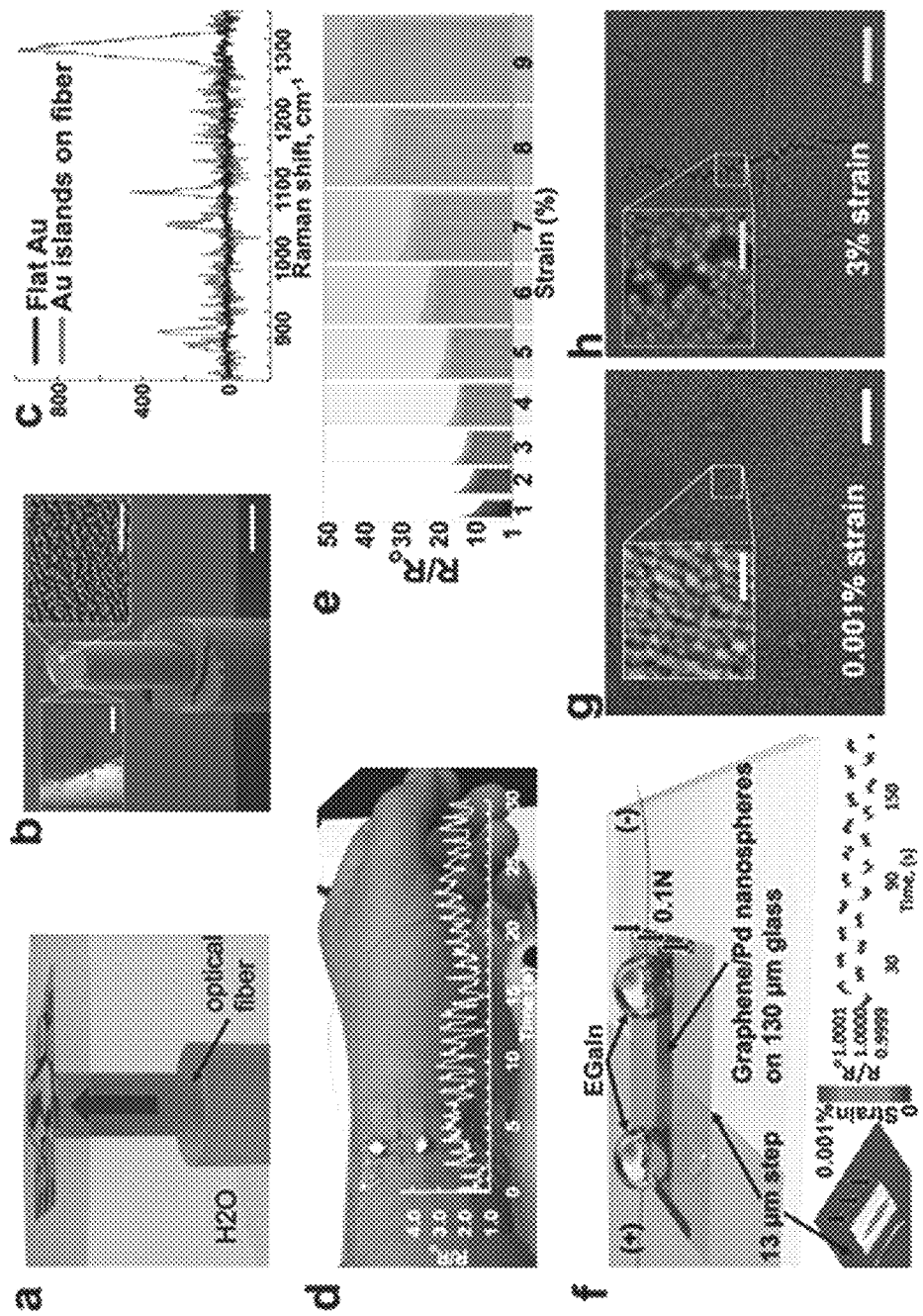
FIG. 3| Applications of nanoislands. a, Schematic diagram of the deposition of free-floating gold nanoislands/graphene SERS substrate onto the tip of the optical fiber. b, Scanning electron micrograph of graphene/AuNI SERS substrate onto the tip of the optical fiber (gold is false-colored). Scale bars: 150 µm, 2 µm in the left inset, 500 nm in the right inset. c, Raman spectra of 1-butanethiolate from graphene/AuNI-coated optical fibers (gray) and unstructured 100 nm-thick gold film (black). d, Photograph of the PDMS/graphene/PdNI strain sensor placed atop the radial artery for detection of the pulse (overlaid in figure). e, Normalized resistance plot of the PDMS/graphene/PdNI strain sensor stretched cyclically (20 cycles for each strain) to 1, 2, 3, . . . 9% strain. f, Schematic diagram of a graphene/PdNI strain sensor used to sense 0.001% tensile strain on the surface of the 130 µm-thick glass coverslip (used as a cantilever with the amplitude of deflection equal to 13 µm). Finite-element analysis (FEA) model of the strain on the cantilever surface (left inset). Normalized resistance plot of the graphene/PdNI strain sensor under cyclic tensile strain of 0.001% (right inset). g, Scanning electron micrograph of the glass/graphene/PdNI strain sensor under tensile strain of ~0.001%. Scale bar: 100 nm. Scale bar in inset: 25 nm. h, Scanning electron micrograph of the PDMS/graphene/PdNI strain sensor under tensile strain of ~3%. Scale bar: 100 nm. Scale bar in inset: 25 nm.

In some embodiments, graphene/AuNI films can be transferred onto tips of optical fibers (as shown in FIGS. 3a and 3b) before a monolayer of 1-butanethiolate (BT) is deposited onto the surface structures formed by the AuNI in the graphene/AuNI films. A large Raman signal was observed from the monolayer of BT deposited on the modified optical fibers. In contrast, BT deposited on an unstructured gold film supported by a silicon layer produced no signal (as shown FIG. 3c). Piezoresistance of composite metal nanoislands on graphene supported by rigid, flexible, or stretchable substrates are highly suitable for use as strain sensors. Examples of rigid substrates include glass, examples of flexible substrates include the polymer poly(methyl methacrylate) (PMMA), examples of stretchable polymer include polydimethylsiloxane (PDMS).

In some embodiments, a highly-sensitive strain sensor capable of measuring a human heart rate epidermally can be fabricated by depositing a thin layer (e.g., 8-10 nm) of metal (e.g., palladium) onto graphene on a metal substrate (e.g., copper substrate) and transferring the composite film structure onto a thin (e.g., about 8 μm) polymer (e.g., polydimethylsiloxane (PDMS)) by spin-coating the polymer. The copper substrate can then be etched to yield highly-sensitive strain sensors (as shown in FIG. 3d). For example, the gauge factor at 1% strain can be at least 1335. Gauge factor $$GF = \frac{R - R_0}{R_0} \frac{1}{\varepsilon},$$

where $\varepsilon$ is strain and $$\frac{R - R_0}{R_0}$$

is the normalized resistance. GF may decrease after several stretch/release cycles. (e.g., 743 after 19 stretch/release cycles, as shown in FIG. 3e).

Strains as small as 0.001% can be measured with a graphene/PdNI sensor deposited onto a 130 μm-thick glass coverslip. Such a small strain can be precisely and repeatedly induced by placing the sensor onto a rigid substrate. The rigid substrate can bear an adhesive tape (e.g., polyimide tape) having a specific thickness (e.g., 13 μm-thick), the tape supporting one half of the coverslip (the other half forming a cantilever) as shown in FIG. 3f. By applying a small force (e.g., ~0.1 N) to the cantilever and bringing the far edge in contact with the substrate, a 0.001% tensile strain (as shown in FIG. 15) on the glass surface can be obtained and measured repeatedly with the sensor.

The graphene/PdNI strain sensors can detect strain spanning at least four orders of magnitude. The sensors can exhibit a nonlinear rate of change in resistance vs. strain (i.e., gauge factor) with at least two inflection points as shown in FIG. 16, which can indicate the presence of different sensing modes.

The piezoresistive effect in the lowest strain regime (~0.001%--~0.1%) is most likely due to the changes in tunneling current when the PdNI undergoes small changes in separation as shown in FIG. 3g. The gauge factor of 10 in this regime is similar to literature values for changes in tunneling resistance at strains <<1%, for example (between 0.02% to 0.27%). The graphene/PdNI films disclosed herein are supported (e.g., on rigid substrates) and thus can be more mechanically robust compared to unsupported sensors prepared by interfacial self-assembly.

At the lower single-digit strains, cracks can appear in the PdNI film (as shown FIG. 3h). PdNI are nanoislands that are spheroidal and that form a film that includes a continuous monolayer of discrete spheroidal nanoparticles.

The opening and closing of these cracks in response to cyclic loading may account for the piezoresistance observed in the most sensitive regime of strains between, for example, 0.1% to 5%. Cycling loading is the repetitive application of force to the sensor resulting in repetitive deformation thereof.

Without being bound of any specific theory, the crack propagation through the PdNI film may be suppressed by the stiffness of the underlying graphene, which can be manifested in the reduction of the gauge factor from 735 to 316 (at 1% and 5% strain, respectively). At around 5-6% strain, the sensitivity can increase again, which can be explained by the crack onset of the underlying graphene (as shown in FIGS. 17, 18, 24) and thus the increased crack propagation through the PdNI film.

The graphene/metal nanoislands composite film structures can be used to monitor a wide variety of samples. For example, monitoring the flexing of an airplane component, such as an airplane wings, cracking of structures, such as a bridges.

The graphene/metal nanoisland composite film structures can also be deployed in biological settings. For example, the performance of graphene/AuNI sensors in biological settings is tested by culturing neonatal rat cardiomyocytes (CM) on coverslips that are coated with a composite polymethylmethacrylate (PMMA)/AuNI/graphene film structure.

Figure 4:
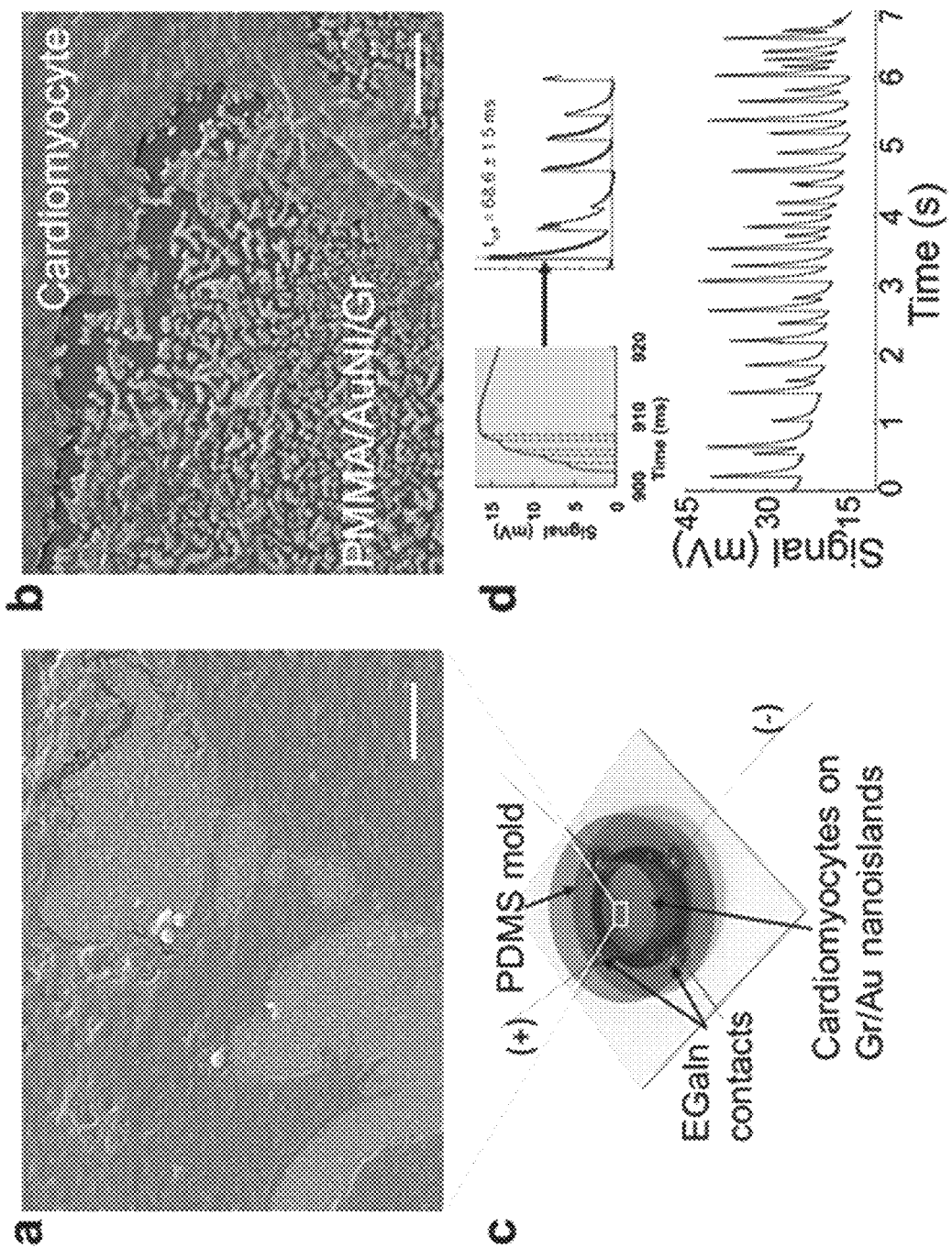
FIG. 4| Nanoislands on graphene as substrates for cellular electrophysiology. a and b, Scanning microscopy images of the fixed cell culture on PMMA/AuNI/graphene substrate (cells are false-colored green and gold is false-colored yellow). Scale bars: 5 µm and 200 nm respectively. c, Schematic diagram of the electrophysiological chamber used for registering cardiomyocyte contractions. d, Signal modulation obtained from the cell culture on PMMA/AuNI/graphene during spontaneous contractions of cells. Profile of the signal rise phase (left inset). Profile of the signal decay phase (right inset).

As shown in FIGS. 4a and 4b, optical and scanning electron microscopy show excellent biocompatibility of the substrates with live CM without the need for additional adhesion promoters. Using a specialized chamber shown in FIG. 4c and detailed below, reversible changes in the sensor signal that correlated with the spontaneous activity of cardiomyocytes can be detected, as shown in FIG. 4d.

An excitation-contraction uncoupler such as blebbistatin, that inhibits myosin cycling and stops the contractions of the cells, but not the electrical activity, can be used to distinguish whether the signal detected by the strain sensor was related to the contractile or electrical activity of the cells. No noticeable modulations of the signal was found in the presence of 10 µM blebbistatin in the solution around the cells, supporting the hypothesis that the sensor responded to contractions and not electrical activities in the cells.

The strain sensors exhibited sub-millisecond (ms) response time (ton=0.8±0.2 ms, n=173), and very high signal-to-noise ratio (between 42 and 100 for CM contractions of different strength) as shown in the top left portion of FIG. 4d. The exponential decay profile was similar for all contractions and was fitted with a single exponential function (toff=68.6±1.5 ms, n=173) as shown in the top right portion of FIG. 4d. The amplitude and the temporal profile of CM contraction as detected by the strain sensor can allow a detailed characterization of CM response and enable testing of various pharmacological compounds for drug discovery applications.

Metallic nanoislands deposited on the surface of graphene—whose morphology can be controlled by the identity of the substrate supporting the graphene and predicted by computation—offer a promising platform system for multimodal sensing. In contrast to films of metallic nanoparticles formed by other procedures, graphene-supported nanoislands have the capacity for manipulation and facile transfer to nearly any surface. Manipulating the graphene-supported nanoislands includes transfer, and also pickup, floatation, alignment, patterning, and placement, for example). This quality can allow mounting of structures directly on the tips of optical fibers for remote sensing by SERS and inserting the optical fibers into these systems such as groundwater or the bloodstream.

Deposition of these structures on relatively rigid (glass), flexible (PMMA), or stretchable (PDMS) substrates permits applications in human and structural health monitoring in which the demonstrated sensitivity can span at least four orders of magnitude and can have the highest gauge factors of any thin-film strain sensor yet reported. The sensitivity and biocompatibility of these structures permit measurement of the contractions of cardiomyocytes non-invasively and can be an invaluable tool for functional characterization of stem-cell derived cardiomyocytes and multi-modal screening of novel drug candidates for cardiotoxicity and cardiovascular drug discovery.

EXAMPLES

Graphene was synthesized on 25-µm-thick copper foils (Alpha Aesar, 13382, 99.8%) with the dimensions of 10 cm×11 cm (graphene sheet as large as 18 cm×20 cm was synthesized and transferred via the metal assisted exfoliation (MAE) described below). Prior to the growth of graphene, the copper foils was cleaned by soaking in a shallow acetone bath and wiping them with a Kimwipe tissue (while in acetone). After that the foils were rinsed with acetone and transferred into a similar bath filled with isopropyl alcohol (IPA), mechanical cleaning was repeated in this solvent. Mechanical cleaning can result in more pristine graphene compared to cleaning the foils via sonication in acetone and IPA. The method can also save a considerable amount of the both solvents (considering the large volumes used for sonicating large-area copper foils). After the mechanical cleaning in IPA, the foils were rinsed in IPA and dried in a stream of compressed air.

Electropolishing the copper foil. Electropolish the copper foils prior to graphene synthesis can help in generating mostly single-layer graphene. The clean, dry copper foil was placed into a 250-mL beaker, following the contours of the beaker side-walls, and was used as the anode. A copper pipe (d=2.54 cm, l=15 cm) was inserted into the beaker along the cylindrical axis and used as the cathode. The cylindrical shape of the cathode and the curved surface of the anode generated a uniform electric field during the electropolishing. Concentrated phosphoric acid ($H_3PO_4$, 15 M) was used as the electrolyte and was poured into the beaker after the cathode and the anode were secured with a clamp and an alligator clip respectively. A 20 W DC power supply can be used to generate the current and voltage. The voltage was set at 1.6 V and electropolishing proceeded until the current fell 50% and plateaued from the initial value (usually between 5-10 min). After the electropolishing, the cathode and the electrolyte were removed from the beaker and the copper foil was extensively rinsed with DI water (3 min). Then the copper foil was rinsed with IPA, blow-dried under a stream of compressed air, and immediately loaded into the middle of the quartz tube of a chemical vapor deposition (CVD) reactor.

Synthesis of graphene. Atmospheric-pressure CVD graphene synthesis was performed in a quartz tube furnace (MTI OTF-1200X-HVC-UL) with the following tube dimensions: d=7.6 cm, l=100 cm. The CVD chamber and the reactor gas-supply lines were purged of air for 5 min by flowing a mixture of all synthesis gases (hydrogen, methane, and argon) at their maximum flow rates while pulling vacuum on the chamber with a diaphragm vacuum pump. After 5 min, the gas flow was stopped and the chamber was evacuated to about $10^{-4}$ torr with a turbomolecular vacuum pump to remove methane and hydrogen from the gas-mixing and the reactor chambers as well as to desorb the possible organic contaminants from the surface of the copper foil, then the furnace was than heated to 730° C. The chamber was then re-pressurized to atmospheric pressure with ultra-high purity argon (700 SCCM), which flowed constantly throughout the entire procedure of graphene synthesis. The copper foils were heated in argon flow to 1050° C. (30 min). Upon reaching this temperature, additional hydrogen (60 SCCM) was flowed for 60 min to anneal and activate the copper substrate. After the 60 min of annealing, the flow rate of hydrogen was reduced to 5 SCCM. After 30 minutes, 0.3 SCCM of methane was flowed for 40 min for the synthesis of graphene (total gas flow rate: 700 SCCM argon+5 SCCM hydrogen+0.3 SCCM methane=705.7 SCCM). After 40 min, the flow rate of methane was increased to 0.7 SCCM. After 60 min of total graphene growth time (with methane flow), the furnace was turned off and cracked open 5 cm (continuing the same gas flow). When the furnace cooled to 700° C. (ca. 5 min) it was opened to 10 cm. At 350° C. (ca. 30 min), the furnace was completely opened. At 200° C., the hydrogen and methane flows were cut off and the reactor chamber was allowed to cool to room temperature in the argon flow (total cooling time was approximately 1 h). The synthesized graphene was analyzed via optical microscopy and a Raman spectromicroscope as shown in FIG. 5. The graphene is of high quality and includes a single-layer with few add-layers. Add-layers are areas of graphene where the number of layers exceeds 1. Upon the completion of graphene synthesis, the copper foil bearing graphene was transferred into an oxygen plasma-treated Pyrex dish (to avoid contaminating the graphene with adventitious adsorbents from the ambient air) and evaporation of metal was immediately performed in a cleanroom environment.

Metal-assisted exfoliation (MAE) Metal-assisted exfoliation (MAE) was used to transfer graphene from copper onto other metals (gold, silver, and nickel). Briefly, graphene is grown on a copper substrate, and then layered on top with a sheet of the other metal (e.g., gold, silver, and/or nickel). Because graphene sticks better to gold than to copper, the entire graphene single-layer can be easily removed and remains intact over large areas. The formation of a conformal graphene/receiving metal interface in the high vacuum environment during MAE can help the interface stay free of oxides and other contaminants. Conformal can include evaporated metal that is in contact with 100% of the graphene surface atoms. For example, graphene on copper can have a significance surface roughness, so conformity can be important to the transfer.

The resultant morphologies after the subsequent nanoisland deposition can then be solely a function of the materials involved (e.g., the evaporant, and the metal substrate) and the processing parameters.

Deposition of metal and self-assembly of NI. To compare the NI morphologies resulting from the selection of the underlying substrate, a Temescal BJD-1800 e-beam evaporator was used to deposit 10 nm of evaporant (gold or silver) onto graphene supported by copper, nickel, gold, and silver. The graphene-bearing substrates were fixed to the sample stage and positioned directly under the source of the evaporant (at distance of 40 cm). The metal evaporation rate was kept low (0.1 Å s$^{-1}$, as monitored by a quartz crystal microbalance) and the chamber pressure was kept at $7\times10^{-7}$ torr during evaporation. The temperature of the substrate at the end of the evaporation was 400 K (also referred to as standard deposition conditions—SDC). The rate of evaporation and the temperature of the substrate can be important parameters that determine the resulting morphology of the NI.

Control evaporations of 10 nm of gold onto graphene supported by copper was conducted at 2 Å/s, 400 K and at 0.1 Å/s, 500 K. Even though graphene offers very low diffusion barriers for gold and silver atoms, the faster rate of evaporation (2 Å/s as opposed to 0.1 Å/s) biases the process to be more kinetically-controlled and results in a less-structured morphology as shown in FIG. S4. Conversely, higher process temperatures (500 K as opposed to 400 K) can result in morphologies of higher crystallinity and lower area coverage as shown in FIG. S5.

All samples were analyzed using the XL30 FEI SFEG UHR scanning electron microscope (SEM). SEM imaging shows that the morphology on the NI depends on the crystallographic orientation of the underlying substrate. FIG. 6 demonstrates the difference in morphology of AgNI resulting from deposition of 10 nm of silver onto graphene on copper substrate (at SDC) with two neighboring copper grains of different orientations. 10 nm of gold at SDC was deposited onto copper substrate bearing graphene with a greater density of add-layers to determine if the number of graphene layers between the substrate and the evaporant influence the NI self-assembly. Further, the copper/graphene/AuNI were coated with 1 μm of Parylene C using a PDS 2010 Parylene coater. Upon etching of the underlying copper, the Parylene/AuNI/graphene was imaged using the SEM (the AuNI were imaged through the underlying graphene). In FIG. S3 it is seen that the amount of percolation on the AuNI decreased on graphene bearing progressively more layers. This correlated well with the model for thin-film growth, since additional graphene layers sequentially lowered the surface energy of copper.

Transfer of graphene/NI films For many applications, NI can be transferred from the substrate upon which they were generated onto the final receiving substrate (optical fiber, glass slide, PDMS, PET, human skin, etc.). The transfer to glass coverslips, silicon wafers and strips of PDMS was performed using standard methodology for transferring graphene. First, the supporting layer of PMMA (e.g., 100 nanometers thick) was spincoated onto copper/graphene/NI, followed by etching of the copper substrate in 1M iron (III) chloride (FeCl$_3$) for 1 hour. After this, the graphene/NI/PMMA film was free floating on the surface of the etchant and was scooped and transferred into a beaker containing deionized water (3 times, 5 minutes in each beaker) to remove contaminants residual from etching the copper. The graphene/NI/PMMA was then scooped with a piece of a silicon wafer for SEM analysis, (FIG. S7).

Strikingly, the morphology of the graphene/AuNI as transferred to the silicon wafer was very different than that before the transfer as shown in FIG. 1. The AuNI formed a completely percolated network and lost sharp crystal edges and corners in favor of rounded features. This effect can be due to substituting (intermittently) the substrate with a high surface area (copper, 1650 mJ/m$^2$) from under graphene/AuNI for water with a low surface energy (72 mJ/m$^2$). The stabilizing substrate crystallinity also disappears with etching of the copper. At this stage, the AuNI apparently reconstruct into the most thermodynamically favorable configuration and likely retain it upon their placement onto the final receiving substrate. The drastic reconstruction can occur in STP conditions. A free-floating film that includes graphene/NI/polymer (FIG. 20) can be deposited onto a substrate in one of two ways, the final receiving substrate interfacing with the graphene or conversely with the supporting polymer. In the first case, the substrate can be first submerged into the DI water and slowly lifted out of the water picking up the floating composite film structure in a Langmuir-Blodgett fashion. Optical fibers, glass coverslips and PDMS strips can be coated in this way for Raman sensing. Rigid substrates and flexible substrate for strain sensing can also be coated this way.

In the second case, the substrate is plunged into the floating graphene/NI/polymer film and further down into the water (FIG. 21). Substrates for cardiomyocyte culture and contraction experiments and well as heart-rate monitoring can be coated in this way. If sensors are supported by PMMA during transfer, this supporting polymer film can be easily removed with acetone. Noticeably, no supporting polymer was used for coating the tips of optical fibers with graphene/AuNI films, as the area of a tip (~0.03 mm$^2$) is significantly smaller than the fragments resulting from breakage of the unsupported graphene/NI film (when such occurs).

In addition to the abovementioned transfer methods, a polymeric film can be laminated on top of the copper/graphene/NI film (e.g. with a commercial laminator) and thus serve as the supporting and final receiving substrate upon copper etching.[8] Such transfer can generate flexible strain sensors supported by 125 μm-thick polyethylterephtalate (PET) (FIGS. 22c,d).

Atomistic Physical Vapor Deposition Simulations. All simulations were performed using the open-source simulation package LAMMPS (Dec. 9, 2014)[9] as available on the Comet supercomputer at the San Diego Supercomputer Center. The simulations were accelerated with a dynamically load-balanced domain decomposition using a message-passing interface distributed on 2 compute nodes containing a total of 48 Intel Xeon processors. A parallel speed up of ~20× corresponding to an efficiency of ~5 ns/day was achieved. Visualization and post-processing analyses were performed using the open-sourced visualization tool, OVITO along with a custom python module.

The initial configuration of the graphene/copper (111) surface was generated and equilibrated following the procedure of Süle et al. Specifically, a 3×3 Moiré super cell with a thick copper support (30 layers) was used as its bottommost layer to effectively model a bulk copper surface. A vacuum layer of height of 4 nm was inserted above the surface to deposit the gold atoms and provide space for the islands to grow. A reflective boundary condition was imposed in the vertical direction with periodic boundaries in the horizontal directions. A schematic of the initial simulation cell is provided in FIG. 25.

Simulated gold deposition. To simulate the deposition process, gold atoms were introduced at random positions within the insertion plane of the vacuum region at a rate of 200 particles per nanosecond with a velocity directed at the surface. This deposition rate was chosen due to computational constraints. Although it is orders of magnitude larger than the experimental rate, the selected rate allows simulations to be performed in a reasonable amount of time with current computational resources and is standard practice throughout the literature. The particle velocities were sampled from the Maxwell-Boltzmann distribution at a temperature commensurate with the experimental evaporation temperature. The temperature of the entire system was maintained at 400 K throughout the deposition process using a Nose-Hoover style thermostat in an NVT ensemble with a time constant of 0.01 ps. The equations of motion were integrated with a time-reversible, measure preserving Verlet algorithm using a time step of 1 femtosecond, which was found to result in numerically stable simulations.

Simulation of thermal annealing. Following the deposition process, the experimental vacuum annealing process was simulated by increasing the temperature to 500 K and allowing the gold islands to diffuse and aggregate until the morphology became stable (~15 ns). During annealing, the surface area of the gold clusters was monitored using the surface mesh modification from the OVITO software package with probe sphere radius of 2.5 Å and a smoothing level of 20.

Due to the hybrid nature of the system, each pair-wise interaction was treated independently with an appropriate interatomic potential. The metal-metal interactions were all computed using the embedded-atom method, which has been extensively used and verified throughout the literature for metallic systems. The carbon-carbon interactions were treated using an AIREBO potential[2], which has been shown to be a good model for graphene. Carbon-copper interactions were treated using an angle-dependent Abell-Tersoff potential, which was parameterized specifically for this system using high level density-functional theory calculations. Finally, the carbon-gold interactions were treated using a Lennard-Jones potential (epsilon=0.0341 eV, sigma=3.003 angstrom), which has been shown to provide an accurate description of the binding and diffusion of gold on graphene, so long as there are no defects or grain boundaries present, as is the case here. A summary of the interatomic potentials used can be seen in Table S1.

Statistical Analysis of Island Growth. The trajectory files output from the physical vapor deposition simulations provide a wealth of information that can be used to quantitatively characterize the morphological evolution and growth of the nanoislands. These metrics provide a basis for comparing different systems and can give insights into the physical mechanisms underlying island growth unattainable from experiments alone. One quantity that can be quite easily monitored is the coordination numbers of the individual gold atoms. Snapshots of the trajectory file was parsed through and all the nearest neighbors were calculated for every gold particle using the bond length as a distance cutoff. FIG. 23 shows the evolution of the probability distribution of the coordination number of the gold particles as the islands grow. These results show that after 0.5 nm of Au has been deposited, the majority of the gold atoms have a coordination number of 6, which corresponds to the surface of the cluster. The majority of the gold atoms have a coordination number of 12 after 1 nm has been deposited, which corresponds to the bulk of the clusters.

Another quantitative metric that can be used to characterize the gold island growth is the distribution of the heights of the gold particles. These were calculated by binning the gold particles from a trajectory snapshot with respect to their vertical heights and normalizing the distribution. FIG. 14 shows the evolution of this probability distribution during the deposition process. With only 0.5 nm Au deposited, a maximum island height is 6 layers (22 Å). This result shows the preference of the gold clusters to bunch up instead of spreading out over the surface, likely due to more favorable gold/gold interactions versus gold/substrate interactions. The above analysis is used to compare the effect of underlying substrate and deposited metal on island growth in future computational experiments.

Optical fiber Raman sensors Unsupported graphene/AuNI was transferred onto tips of freshly-cleaved 300 μm-thick optical fibers (core: 50 μm in radius, 50 μm-thick cladding, 50 μm-thick sheath) to study the feasibility of using the graphene/NI composite film structures as SERS substrates for label-free sensing. 7.5 nm of gold was evaporated onto graphene on copper to obtain non-percolated AuNI with minimal gaps (e.g., between 3-20 nm) between them (FIG. 3b, right inset). 7.5-8 nm of Au deposition is established as the percolation threshold for AuNI. After transferring the films and drying the fibers overnight in ambient air, they were placed into a beaker containing a 10 mM ethanoic solution of 1-butanethiol (BT) together with a 1 $cm^2$ piece of a silicon wafer with an evaporated 100 nm-thick film of gold (as a control substrate) to form a self-assembled monolayer (SAM) of BT on gold surfaces. At this thickness, gold is not transparent so the identity of the substrate $SiO_2$ or $Si/SiO_2$ is not important.

After 24 hours, the test substrates were thoroughly rinsed in DI water and isopropanol (IPA) and dried in ambient air.

Raman spectroscopy analysis. For obtaining the Raman spectra from the test substrates, a Raman microscope (Renishaw inVia) with an inverted stage and with a 785 nm excitation source was used. For both test samples and the control, the laser beam was focused to a 2 μm beam spot and the exposure was set to 60 seconds at 0.5 mW power. Distinct BT signals was obtained from the tips of the coated optical fibers (albeit with a low signal-to-noise ratio) even at as low as one second exposure, while no BT signal was obtainable at 60 s exposure even by raising the beam power to 5 and then to 50 mW. This indicates that graphene/AuNI are suitable SERS substrates and far superior to unstructured gold films. This embodiment demonstrates the manipulability of the composite graphene/NI film structures. They can be transferred on a tiny object like a tip of the optical fiber, allowing for the very promising application in remote sensing.

Graphene/PdNI films as strain sensors. Depositing ~10 nm of Pd onto graphene on copper under SDC resulted in formation of a uniform monolayer of spherical particles (4-5 nm in diameter). These spherical particles, even though of a very different shape, is still a function of the materials selection and can be fabricated in the same way as other nanoislands disclosed herein. These graphene/PdNI were then transferred onto rigid (glass), flexible (PET) and stretchable (PDMS) substrates (FIG. 22) to test their piezoresistive properties over large range of strains.

PdNI sensors on rigid substrates. To evaluate the performance of PdNI as strain sensors under very low strains <<1%, 3-5 by 25 mm graphene/PdNI/PMMA strips were transferred onto 1" by 1" glass coverslips that were 130 μm thick. To remove PMMA, the slides were rinsed with acetone. To electrically address the sensor, copper wires (36 gauge) were adhered to the PdNI and glass coverslips with copper tape bearing conductive adhesive and drops of EGaIn were placed on the loose wire ends to ensure a stable electrical contact FIG. 22a. In all cases the aspect ratio of PdNI sensors after the attachment of electrodes can be between 3 and 10 and unstrained resistance between 644 and 2015 Ohms.

To induce and register very small strains (0.001%-0.003%) with PdNI sensors, 13 μm-thick polyimide (PI) tape (1 layer for 0.001% and 3 layers for 0.003% strain) was placed onto a 2" by 3" glass slide. PI tape was used as a step of controllable height to create a cantilever by resting and fixing one half of the PdNI-coated glass coverslip on the tape while creating a gap between the coverslip and the glass slide under the other half of the coverslip (FIG. 3f). By applying a small force (~0.1 N) to the free end of the cantilever and bringing it in contact with the glass slide, the glass slide is bent, inducing tensile strains on its PdNI-coated surface and registered the resistance change with a Keithley 2400 source/meter using a custom-generated Lab-VIEW code (FIG. 3f, right inset). Solid Pd film control samples were analyzed in a similar fashion (FIG. 19).

PdNI sensors on stretchable substrates. To measure the piezoresistivity of PdNI sensors at higher strains (>1%), the PdNI sensors were transferred onto strips of PDMS (3 mm by 10 mm by 100 mm), addressed them with copper wires and EGaIn (eutectic gallium indium), and used a high-precision linear actuator to stretch the PDMS (FIG. 22b). Graphene (without PdNI) control samples were analyzed in a similar fashion. The sensors were cycled between 0% and 9% strain at 1% intervals (20 cycles per each 1% interval) (FIG. 3e). The sensors exhibited very high gauge factors and cyclability while maintaining a stable baseline (FIG. 24).

Heart rate measurements. To obtain biometric signals, 8 μm-thick PDMS films were spincoated on copper/graphene/PdNI, and the PDMS was cured on a hotplate at 100° C. for 10 minutes. The copper was etched in 1M iron (III) chloride for 1 hour. The free-floating graphene/PdNI/PDMS films was transferred into DI water (3 times) and deposited the sensor onto the skin on the wrist (on top of the radial artery) (FIG. 3d) by plunging the wrist into the vessel with the DI water and the sensor.

Being hydrophobic, the PDMS surface formed a good interface with the skin. Prior to depositing the sensor, a strip of an adhesive tape was adhered around the wrist while leaving a section of the skin above the radial artery tape-free. The adhesive tape served two purposes: it helped the attachment and keeping in place of the electrical contact wires and localized the strain on the tape-free section of the skin by rendering the tape-covered skin unstretchable. One sensor was able to measure the heartrate while two other sensors generated wrinkles in PDMS during the transfer process and were not sensitive enough (although all three sensors were able to register wrist and individual digit motions with a high fidelity).

In-situ SEM on PdNI sensors. To register the film morphology of PdNI sensors under 0.001%, 3%, and 5% strains, the sensors were imaged with the XL30 FEI SFEG UHR scanning electron microscope. To image the sensors under small strains on the rigid substrate, the PI tape step methodology was used. Here, instead of applying intermittent force on the cantilever, the free end of the cantilever was permanently taped to the glass slide with a conductive copper tape. This tape also served as an electrical ground electrode to discharge the sample to the SEM stage.

For obtaining the images of the sensor films under 3% and 5% strain, the sensors supported by 1 mm-thick PDMS strips were adhered to the curved surfaces of 3D-printed half-cylinders with the radii of curvature of 15 mm and 10 mm respectively (bending PDMS strips to the specified radii generated surface tensile strains of 3 and 5%) by using the adherent copper tape that also served to electrically ground the samples to the SEM stage.

Electrophysiology. Neonatal rat ventricular cardiomyocytes were isolated using the neonatal rat cardiomyocyte isolation kit (Worthington) and cultured at 37° C. with 5% $CO_2$. In brief, ventricles were dissected from 1 d-old Hsd: SD rats (Sprague Dawley), then digested overnight at 4° C. with trypsin. Digestion continued the following morning with collagenase for approximately 60 min at 37° C. Cells were pre-plated for 90 min to remove fibroblasts, and plated on 12 mm glass coverslips coated with PMMA/AuNI/graphene in high-serum media (DMEM/F12 [1:1], 0.2% BSA, 3 mM sodium-pyruvate, 0.1 mM ascorbic acid, 4 mg/liter transferrin, 2 mM L-glutamine, 100 nM thyroid hormone (T3) supplemented with 10% horse serum and 5% fetal bovine serum) at $2 \times 10^5$ cells/cm$^2$. After 24 h, media was changed to low-serum medium (same as above but with only 0.25% fetal bovine serum). Three cell cultures were plated on PMMA/AuNI/graphene with at least 8 substrates in each cell culture. Several PMMA/AuNI/graphene substrates were coated with Matrigel in each cell culture plating to compare the adhesion of cells to bare PMMA/AuNI/graphene substrates and those coated with Matrigel. No difference in cell adhesion and viability between the samples was observed.

Scanning Electron Microscopy. First, cells were washed with 0.1 M phosphate buffer (pH 7.4), then fixed with 4% formaldehyde solution for 2 hours at room temperature, and washed with the same buffer three times for 5 min each. Following dehydration with graded series of alcohol (30% ethanol—10 min, 50% ethanol—10 min, 70% ethanol—10 min, 80% ethanol—10 min, 95% ethanol—2 changes in 10 min, 100% ethanol—3 changes in 15 min), all samples were freeze dried in a vacuum chamber, and coated with sputtered iridium. Scanning electron microscopy images were acquired on the XL30 FEI SFEG UHR at the working distance of 5 mm while using the 10 kV energy beam.

Electrophysiological measurements. A custom electrophysiology chamber was built by 3D printing a mold in which PDMS (Sylgard 184) was cured. The finished chamber had a central opening (for cell culture and media) and side openings (for eutectic electrode placement) and was placed on top of the glass coverslips bearing PMMA/AuNI/graphene and CM culture in a way that the central portion of the AuNI substrate was located in the central opening and the edges of the AuNI substrate were accessible for electrical addressing using EGaIn through the side openings (FIG. 4a). The assembly was then sandwiched between two 1" by 3" glass slides and clamped with binder clips to ensure a good seal. A 5 mm aperture was pre-drilled in the top glass slide to allow adding media and blebbistatin to the central opening of the chamber. The PDMS walls between the camber openings served to separate the EGaIn electrodes from the cell media (in mM, NaCl, 135; KCl, 2.5; $CaCl_2$, 2; $NaHCO_3$, 1; $Na_2HPO_4$, 0.34; $KH_2PO_4$, 0.44; glucose, 20; and HEPES, 10 (pH 7.4). Electrophysiological recordings were performed in current-clamp configuration using a Digidata 1322 interface, an Axopatch 200B amplifier, and pClamp software (Molecular Devices Corp.). The data were digitally sampled at 50 kHz and filtered at 2 kHz. Experiments were performed at room temperature. Blebbistatin (10 uM, Tocris), and KCl (30 mM) were added directly to the experimental chamber to affect the rate of CM contractions. All traces representing individual contractions were fitted with exponential functions using Clampfit10.3 and OriginPro2015.

TABLE S1

Summary of interatomic potentials used in this study.

| Interaction Pair | Interatomic Potential |
|---|---|
| Carbon-Carbon | AIREBO[20] |
| Carbon-Copper | Abel-Tersoff Potential[13] |
| Carbon-Gold | Lennard-Jones[22] |
| Copper-Copper | Embedded Atom Method[25] |
| Copper-Gold | Embedded Atom Method[26] |
| Gold-Gold | Embedded Atom Method[19] |

The methods and systems disclosed herein can also provide electrical impedance profile of the activity of cells (e.g., cultured cells). The general equation for an impedance is $Z=R+jX$, where R is a "common" resistance, and an imaginary part jX relates to phase shift of the reactance of the circuit. Impedance can be relevant for an AC current measurements. For DC current measurements, impedance equals resistance of the circuit. Using impedance over resistance recordings can allow additional information to be collected via an extra component of cells behavior related to a phase-shifted capacitance discharge-recharge of the electrodes.

In general, impedance adds a frequency-domain ratio of changing voltage to a changing current. A way to measure an impedance profile for contracting cells (e.g., contracting cultured cells) may include two electrodes on opposite sides of the cell layer. The systems can include a recording circuitry having a number of electrodes, where at least one of the electrodes is located on each side of the cell layer.

For example, impedance measurements can be collected with an electrophysiology-like amplifier, which is capable of recording fast current-voltage signals in a time-resolved manner.

When cells (e.g., cultured cells) cover an electrode, the electrical impedance between the electrode and the solution can increase. As they contract (i.e., area is shrinking), the exposed electrode area increases and impedance drops, thus registering a beat (and its amplitude).

The systems and methods disclosed herein can measure several parameters, including the first derivative of voltage profile over the cellular membrane capacitance. Cell membrane potential is a voltage difference between an inner (cytosolic) leaflet and an outer (extracellular) part of the cell membrane. When electrodes contact the cell membrane, activities (e.g., contractile activities) of cells (e.g., cultured cells) can be traced via monitoring a cellular membrane potential profile. For example, the systems and methods disclosed herein can measure several components of voltage dynamic changes due to the cellular activity.

The systems and methods herein can provide a profile of cellular contractility by optical observation of the interparticle distance change between the nanoislands, for example, using dark-field microscopy. Dark-field microscopy can include an illumination technique that enhances image contrast. The illumination light can be very strong, and after the illumination of the sample, the direct illumination light beam is blocked from entering an objective used to view the sample. As a result, the only light that enter the objective lens would be scattered light from the sample. This microscopy technique produces an almost black background with bright shiny images against the dark background.

Sizes of nanoislands can be less than a diffraction limit for light microscopy. However, with larger sized islands (e.g., much bigger) and effect caused by a localized surface plasmon resonance, dark-field images can be detected.

Advantages of such a system would be the ease of tracking and analyzing the metallic nanoislands. Cells, such as the cultured cardiomyocytes, can apply a contractile force to the nanoislands and shift them around. The amount of shift and other parameters (color changes/light wavelength change) can be used for detection.

The methods and systems disclosed herein can be configured to provide the profile of cellular contractility by optical observation of calcium ion concentration. The dynamics of calcium ions concentration change inside cardiomyocytes can be used to detect cardiomyocytes activity. For example, by the use of specially formulated fluorescent calcium indicator dyes. Each dye molecule can change its fluorescence upon binding a calcium ion. This dye should be loaded inside the cultured cells (e.g., cardiomyocyte cells or any other cell type) prior to recording, for example, by conventional fluorescent microscopy. Elevation of calcium concentration inside cells can initiate actin/myosin coupling which results in a cellular contraction. Thus, the dynamic changes of intracellular calcium concentrations (as opposed to the ions near metallic nanoislands) can be an adequate "surrogate measure" of the cellular contractile activity. The recorded signal can be fast and bright, with a good dynamic range.

The methods and systems disclosed herein are configured to provide Raman scattering data from the cultured cells. The Raman spectrum data from cells is an addition to the main sensor modality. Raman signal from biochemically active structures on the cellular surface may be able to reflect changes in membrane chemical compositions during contractile activity.

Since cells can be in direct contact with the plasmonically active nanoislands (e.g., gold islands), the latter can enhance the Raman signal from the expressed membrane proteins, cellular analytes, cytokines, etc., as well as chemistry some tens of nanometers into the cell body. Since the methods and systems disclosed herein are orders of magnitude more plasmonically active than an unstructured gold film, in which mitochondrial motion was detected, the resolution and signal to noise ratio of the disclosed systems can be greater. Data analysis can include deconvolution of the obtained complex signal from the cell biochemistry.

The systems and methods disclosed herein can be configured to stimulate cellular activity electrically. A way to stimulate cells electrically can include using two separate electrodes on both sides of the cell layer and apply a voltage between these two electrodes. The methods and systems disclosed herein can be used as passive electrodes, with one electrode above and one below the cells.

The methods and systems disclosed herein can stimulate cellular activity optically. For example, gold nanoislands can be plasmonically active and can stimulate cellular contraction using one band of light while permitting to get the optical cellular activity readout by another band of light. For example, when light is shone on cells grown on nanoislands (e.g., gold islands), they can contract much faster. With significant illumination, they go into tetanus (state of continuous contraction). Light may activate plasmonics modes in the gold islands and change the electric fields on the surface and in the gaps. This may cause cell membrane depolarization and cell activity.

The methods and systems disclosed herein can include wearable sensors to the skin or clothing. The applications for such systems can include healthcare, wellness, haptic technology, instrumented prostheses, and other applications in which the nanoisland sensors are used external to the body.

A number of embodiments of the invention have been described. Nevertheless, it will be understood that various modifications may be made without departing from the spirit and scope of the invention. Accordingly, other embodiments are within the scope of the following claims.

What is claimed is:

1. A method for fabricating a composite film structure, the method comprising:
   determining a desired morphology for a metallic layer of the composite film structure;
   selecting a first metal substrate based on the determining;
   transferring a graphene layer onto the first metal substrate;
   depositing the metallic layer on the graphene layer to achieve the desired morphology, wherein a surface energy difference between the first metal substrate and the deposited metallic layer results in the desired morphology of the metallic layer, the desired morphology comprises a layer of nanoislands having controlled and uniform inter-nanoisland separation and a distance between edges of nanoislands in the metallic layer is on the order of about 2 Å to a few nanometers, and
   removing the first metal substrate from the graphene and the deposited metallic layer to form the composite film structure.

2. The method of claim 1, wherein depositing the metallic layer comprises deposition of evaporated flux of metallic atoms.

3. The method of claim 2, wherein the evaporated flux of metallic atoms self-assemble to yield the desired morphology.

4. The method of claim 2, where in the evaporated flux of metallic atoms are produced by electron beam evaporation, thermal evaporation, or sputtering.

5. The method of claim 1, wherein transferring the graphene layer onto the first metal substrate comprises exfoliating the graphene grown on a second metal substrate and placing the graphene layer onto the first metal substrate; and wherein the graphene comprises a single layer of graphene.

6. The method of claim 5, wherein the graphene is grown on the second metal substrate using chemical vapor deposition.

7. The method of claim 1, wherein the first metal substrate comprises a transition metal.

8. The method of claim 7, wherein the transition metal comprises gold, silver, or nickel.

9. A method of forming a substrate for surface-enhanced Raman scattering, the method comprising:
   depositing a graphene layer on a first metal substrate;
   depositing a plurality of metallic nanoislands on the graphene layer, wherein a surface energy difference between the first metal substrate and the deposited metallic nanoislands results in the desired morphology of the metallic nanoislands, the desired morphology comprises a layer of nanoislands having controlled and uniform inter-nanoisland separation and a distance between edges of nanoislands in the metallic layer is on the order of about 2 Å to a few nanometers; removing the first metal substrate from the graphene and the deposited plurality of metallic nanoislands to form the substrate for surface-enhanced Raman scattering.

10. A method of performing surface-enhanced Raman scattering of an analyte, the method comprising:
    forming a substrate for surface-enhanced Raman scattering according to the method of claim 9;
    transferring the substrate on an optical fiber;
    coating the analyte on the substrate; and
    recording surface-enhanced Raman scattering signals from the analyte.

11. The method of claim 10, wherein the plurality of metallic nanoislands comprises a plasmonically active metal.

12. The method of claim 11, wherein the plasmatically active metal comprises copper, silver, palladium, gold, or platinum nanoislands.

13. A method of performing surface-enhanced Raman scattering of an analyte, the method comprising:
    forming a substrate for surface-enhanced Raman scattering according to the method of claim 9;
    transferring the substrate on an optical fiber;
    placing the substrate into the analyte; and
    recording surface-enhanced Raman scattering signals from the analyte.

* * * * *